United States Patent [19]
Cartilier et al.

[11] Patent Number: 5,879,707
[45] Date of Patent: Mar. 9, 1999

[54] SUBSTITUTED AMYLOSE AS A MATRIX FOR SUSTAINED DRUG RELEASE

[75] Inventors: Louis Cartilier, Beaconsfield; Iskandar Moussa, Montreal; Chafic Chebli, Dollard des Ormeaux; Stéphane Buczkowski, Montreal, all of Canada

[73] Assignee: Universite De Montreal, Montreal, Canada

[21] Appl. No.: 739,539

[22] Filed: Oct. 30, 1996

[51] Int. Cl.⁶ .............................. A61K 9/22; A61K 47/36
[52] U.S. Cl. ............................................. 424/468; 514/960
[58] Field of Search .................................... 424/488, 468; 514/778, 960, 60; 525/54.31; 536/102, 120

[56] References Cited

U.S. PATENT DOCUMENTS

| | | |
|---|---|---|
| 3,034,911 | 5/1962 | McKee . |
| 3,490,742 | 1/1970 | Nichols et al. . |
| 3,622,677 | 11/1971 | Short et al. . |
| 4,072,535 | 2/1978 | Short et al. . |
| 4,369,308 | 1/1983 | Trubiano . |
| 4,985,082 | 1/1991 | Whistler . |
| 5,108,758 | 4/1992 | Allwood et al. . |
| 5,455,342 | 10/1995 | Redding, Jr. . |
| 5,456,921 | 10/1995 | Mateescu et al. . |
| 5,585,114 | 12/1996 | Besemer et al. . |

FOREIGN PATENT DOCUMENTS

| | | |
|---|---|---|
| 499648 | 6/1992 | European Pat. Off. . |
| 9402121 | 1/1994 | WIPO . |
| 9421236 | 3/1994 | WIPO . |

OTHER PUBLICATIONS

Salomon et al., Pharm. Acta Helv., 55, 174–182, (1980).
Buri P. et al, Pharm., Acta Helv. 55, 189–197 (1980).
Kost J. et al., Biomaterials, 11, 695–698, (1990).
Biliaderis C., Can. J. Physiol. Pharmacol. 69, 60–78, (1991).
Mateescu M. et al, Biochimie, 58, 875–877, (1976).
Nakano M. et al, Chem. Pharm. Bull. 35, 4346–4350, (1987).
Van Aerde P. et al, Int. J. Pharm., 45, 145–152, (1988).
Hermann J. et al, Int. J. Pharm., 56, 51–63 & 65–70, (1989) and Int. J. Pharm., 63, 201–205, (1990).
Dumoulin et al., Inter. Symp. Control. Rel. Bioact. Mater, 20, 306–307, (1993).
Lenaerts V. et al, J. Controlled Rel. 15, 39–46, (1991).

*Primary Examiner*—Edward J. Webman
*Attorney, Agent, or Firm*—Bacon & Thomas, PLLC

[57] ABSTRACT

A pharmaceutical sustained release tablet for oral administration is made of a compressed blend of at least two dry powders including a powder of a pharmaceutical drug and a powder of a sustained release matrix for the drug. The sustained release matrix is made of substituted amylose prepared by reacting, in a basic medium, amylose with an organic substituent having a reactive function that reacts with the hydroxy groups of the amylose molecule. This substituent is preferably an epoxy or halogen alkane or alcohol with such a matrix controlled and sustained release of a drug are achieved with a remarkable close-to-linear profile and a release time of from 9 to 20 hours.

20 Claims, 28 Drawing Sheets

- Fraction of Acetaminophen Released from SA,G-0.4 Tablets

A-

B-

Figure 1- Amylose chemical structure
    (A) 3-D presentation, (B) 2-D presentation (A) SUBSTITUTION THROUGH AN EPOXIDE FUNCTION (B) SUBSTITUTION THROUGH A HALIDE LEAVING GROUP (C) SUBSTITUTION THROUGH AN ISOCYANATE GROUP (D) SUBSTITUTION THROUGH PHOSPHORUS OXYCHLORIDE FIG. 13 — The Effect of Drug Loading on the Fraction of Acetamin. Released from SA,G-2.7 Tablets FIG. 14 - The Effect of Drug Loading on the Time of 100% Acetamin. Release from SA,G-2.7 Tablets

SUBSTITUTED AMYLOSE AS A MATRIX FOR SUSTAINED DRUG RELEASE

FIELD OF THE INVENTION

The present invention relates to a sustained release solid dosage unit.

More specifically, the invention relates to a pharmaceutical tablet comprising substituted amylose as a matrix for sustained release of the drug contained in the tablet.

BRIEF DESCRIPTION OF THE PRIOR ART

Drug controlled release system

For many years, one of the major axes in pharmaceutical research has been the synthesis of new active ingredients of improved therapeutic efficiency. Though this continues to be a fundamental trend, increased attention has also been given to controlling drug administration characteristics or pharmacological activity. Consequently, this has led to the development of new pharmaceutical dosage forms allowing control of drug release.

Among the many oral dosage forms that can be used for the controlled release of drugs, tablets are of major interest in the pharmaceutical industry because of their highly efficient manufacturing technology.

Many systems have been proposed to control drug release in a tablet. In such systems, drug release is controlled by diffusion, solvent activation, polymer swelling, chemical reaction or osmosis. Most of the time, use is made of combination of two or more mechanisms which obey the Fick's laws [Ségot-Chicq S. et al, S.T.P. Pharma, 1, 25–36 (1985)].

Several types of polymers have been proposed so far for use as a matrix for the controlled release of drugs. Examples of such polymers are poly(vinylpyrrolidone), poly (vinylalcohol), poly(ethylene oxide), cellulose and its derivates, silicone and poly(hydroxyethylmethacrylate) [Korsmeyer R., Diffusion controlled systems: hydrogels, chap. 2, pp. 15–37 in Polymers for controlled drug delivery, Ed. Tarcha p., CRC Press, Boca Raton, USA, 1991; Salomon et al., Pharm. Acta Helv., 55, 174–182, (1980); Buri P. et al., Pharm. Acta Helv. 55, 189–197 (1980)].

Characteristics of an ideal drug controlled release system

In spite of all the existing systems, there is still a need for an "ideal" drug controlled release system which would allow a constant release of the drug and would be easy to manufacture.

Matrix tablets obtained by direct compression of a mixture of a drug with a polymer would be the simplest way to achieve this goal. Preferably, these tablets should also show good mechanical qualities (i.e. tablet hardness and resistance to friability) in order to meet the manufacturing process requirements and the subsequent handling and packaging requirements. Furthermore, the obtained polymers used as matrices should be easy to synthesize, a one step procedure being an ideal case. The obtained polymers should also be biocompatible, biodegradable and non toxic, with the proviso that biodegradable synthetic polymers have the disadvantage of a possible toxicity following absorption of the degraded products.

Polysaccharidic biodegradable matrices

Polysaccharidic biodegradable matrices for tablets are of interest because the degradation of a natural product like starch occurs naturally in the human body [Kost J. et al., Biomaterials, 11, 695–698, (1990)].

Starch is composed of two distinct fractions, consisting of (1) amylose which is a non-ramified fraction containing about 4,000 glucose units and (2) amylopectin which is a branched fraction containing about 100,00 glucose units [Biliaderis C., Can. J. Physiol. Pharmacol. 69, 60–78, (1991)].

Starch and cross-linked starch obtained by treatment with reagents like epichlorohydrin, phosphorous oxychloride, adipic anhydride, etc. are widely and safely used with the agreement of the Food and Drug Administration in the food industries (thickener, enhancer of organoleptic properties, texture modifier . . . ) and in the pharmaceutical industry (filler, binder, disintegrant) [see again Biliaderis C., Can. J. Physiol. Pharmacol. 69, 60–78, (1991)].

Starch is naturally hydrolysed by several amyollytic enzymes. Hence, α-amylase is an endoenzyme specific to α-(1,4)-D-glucopyranosidic bonds located within polyglucose chains. The degradation product of starch amylolysis is mainly composed of oligosaccharides, dextrins and maltose [Mateescu M. et al., Biochimie, 58, 875–877, (1976)].

Unmodified, modified, derivatized or cross-linked starches

Short et al. [U.S. Pat. Nos. 3,622,677 and 4,072,535] disclose a binder/disintegrant consisting of a starch physically modified by compaction. The starch used as starting material may be any granular starch derived from the root, stem or fruit of a plant. It may be modified, derivatized or cross-linked. However, no controlled release properties are described. Furthermore, these patents do not disclose or suggest the specific role of amylose present in starch, nor do they disclose or suggest the use of amylose to improve the binding properties of the material.

Trubiano [U.S. Pat. No. 4,369,308] discloses modified starches which are low swelling in cold water and which are suitable for use as disintegrants in compressed tablets. This goal is achieved by cross-linking and pregelatinizing, in the presence of water, a cold-water-insoluble, granular starch, drying the cross-linked, pregelatinized starch if necessary, and then pulverizing the dry starch. Once again, no controlled release properties are disclosed for these starches and the specific role of amylose present in starch is not discussed nor in its use to improve the disintegrating properties of the tablets.

McKee I. [U.S. Pat. No. 3,034,911] discloses a method of producing cold water-soluble, intact granular starches such as starch phosphate, starch sulphate and carboxymethylstarch, by chemical derivatization of starch. The granular starches that are so-produced are only used in tablets as disintegrants. No controlled release properties are disclosed.

Nakano M. et al. [Chem. Pharm. Bull. 35, 4346–4350, (1987)] disclose the use of physically modified starch (pregelatinized starch) as an excipient in sustained-release tablets. This article does not mention the specific role of amylose present in starch nor does it even mention amylose.

Van Aerde P. et al. [Int. J. Pharm., 45, 145–152, (1988)] disclose the use of modified starches obtained by drum-drying or extrusion pregelatinization, particle hydrolysis or cross-linking with sodium trimetaphosphate, as an excipient in sustained-release tablets. Once again, the article does not mention the specific role of amylose present in starch nor does it even mention amylose.

Hermann J. et al. [Int. J. Pharm., 56, 51–63 & 65–70, (1989) and Int. J. Pharm., 63, 201–205, (1990)] disclose the use of thermally modified starches as hydrophillic matrices for controlled oral delivery. This article discloses that thermally modified starches containing a low amount of amylose (25% and lower) give good sustained release properties, contrary to high amylose content starches which present bad controlled release properties. Hence, the role of amylose present in starch is considered negatively.

Non-granular, glassy and "short-chain" amylose

Nichols et al. [U.S. Pat. No. 3,490,742] disclose a binder-disintegrant comprising non-granular amylose. This material is prepared either by fractionating starch or by dissolving granular high amylose starch in water at an elevated temperature. No controlled release properties are disclosed.

Alwood, et al. [U.S. Pat. No. 5,108,758] disclose an oral delayed release composition comprising an active compound and glassy amylose. The composition is particularly adapted for achieving selective release of the active compound into the colon. The delayed release is due to a coating. Glassy amylose is one of the two forms of predominantly amorphous amylose, the other being a rubbery form. Here, the glassy amylose delays the release of the active compound from the composition in an aqueous environment but allows its release on exposure to an enzyme capable of cleaving the amylose. The amylose used in this composition is isolated from smooth-seed pea starch and purified by precipitation from aqueous solution as a complex with n-butanol. The alcohol is then removed from an aqueous dispersion of that complex by blowing through a suitable heated inert gas. As aforesaid, the release mechanism is based on an enzymatic reaction. There is no continuous release through the gastrointestinal tractus, but only a delayed release due to the degradation of the coating into the colon. Moreover, it is disclosed that the glassy amylose should preferably not contain hydroxy groups in a derivative form.

Wai-Chiu C. et al. [see European laid-open patent application No. EP-A-499,648] disclose a tablet excipient. More particularly, they disclose a starch binder and/or filler useful in manufacturing tablets, pellets, capsules or granules. The tablet excipient is prepared by enzymatically debranching starch with an alpha-1,6-D-glucanohydrolase to yield at least 20% by weight of "short chain amylose". No controlled release properties are claimed for this excipient. Moreover, starch (unmodified, modified or cross-linked) must be enzymatically treated with an $\alpha$-1,6-D-glucanohydrolase to be debranched and to yield the so-called "short chain amylose". Thus, starch with a high content of amylopectin is obviously preferred and amylose is rejected as not suitable because it is impossible to debranch amylose, since amylose has no branching. The role of amylose is not only ignored but considered negatively.

In connection with this reference, it must also be emphasized that "short-chain amylose" does not exist. In the present specification and appended claims, when the term "amylose" is used, it refers only to amylose having a long chain consisting of more than 250 glucose units (between 1000 and 5000 units according most of the scientific literature), joined by $\alpha$-1,4-D glucose links, in a linear sequence. This is totally different from short chains of 20 to 25 glucose units. In each case, the three-dimensional structure is completely different thereby explaining why one obtains different behaviours.

Cross-linked amylose

Mateescu M. A. et al. [U.S. Pat. No. 5,456,921] and Lenaerts V. et al. [J. Controlled Rel. 15, 39–46, (1991)] disclose that cross-linked amylose is a very efficient tool for drug controlled release. Cross-linked amylose is produced by reaction of amylose with a cross-linking agent such as epichlorohydrin, in an alkaline medium. Different degrees of cross-linking can be obtained by varying the ratio of epichlorohydrin to amylose in the reaction vessel. Tablets prepared by direct compression of a dry mixture of cross-linked amylose and a drug swell in solution and show a sustained release of the drug. Depending on the degree of cross-linking of the matrix, different degrees of swelling are obtained. However, with degrees of cross-linking above 11, the swollen polymeric matrix presents in vitro disintegration over a period of approximatively 90 minutes. Increasing the degree of cross-linking of amylose generates an increase of drug-release time, with maximal values for low degrees of cross-linking. A further increase in the degree of cross-linking leads to an accelerated drug release from the cross-linked amylose tablets as a consequence of the erosion process.

Mateescu M. A. et al. [International laid-open patent application No. WO 94/02121] and Dumoulin et al. [Intern. Symp. Control. Rel. Bioact. Mater. 20, 306–307, (1993)] disclose an enzymatically-controlled drug release system based on the addition of $\alpha$-amylase to cross-linked amylose in a tablet, so as to modulate the release kinetics of the drug. The $\alpha$-amylase within the tablet is able to hydrolyse $\alpha$-1,4-glucosidic bonds present in the cross-linked amylose semi-synthetic matrix. Increasing amounts of $\alpha$-amylase (5 to 25 EU) within the tablets induce a significant decrease in release time from 24 to 6 hours. Hence, drug release is controlled by two sequential mechanisms: (a) hydration and swelling of cross-linked amylose tablets followed by (b) internal enzymatic hydrolysis of the hydrated gel phase.

Cartilier L. et al. [International laid-open patent application WO 94/21236] disclose powders of cross-linked amylose having a specific cross-linking degree for use as a tablet binder and/or disintegrant. The tablets are prepared by direct compression. The concentration of cross-linked amylose in the tablets is lower than 35% by weight. Degrees of cross-linking from 6 to 30 and more particularly from 15 to 30 are preferred when disintegration properties are required.

All these patents, laid-open applications and articles relate to the use of cross-linked amylose, which should not be confused with linearly substituted amylose. The swelling and drug release time of the tablets made of cross-linked amylose depend strongly on the degree of cross-linking and show a very specific behaviour pattern which is totally different from the one obtained in accordance with the present invention.

SUMMARY OF THE INVENTION

It has now been discovered that substituted amylose is a very interesting excipient for the preparation of drug controlled release tablets. The advantages of such excipient are numerous, and include in particular:

1. very easy synthesis;

2. easy manufacturing of the tablets by direct compression, 3. possibility of a large range of drug concentration in the tablet, 4. versatility of the matrix, which is hydrophilic;

5. good mechanical properties of the tablets by direct compression; and 6. safety of substituted amylose.

More particularly, it has been found that controlled and sustained release of a drug can be achieved when use is made of substituted amylose as a matrix in a tablet, with a remarkable close-to-linear profile and a release time of from 9 to 20 hours.

In accordance with the invention, there is provided a pharmaceutical sustained release tablet for oral administration, consisting of a compressed blend of at least two dry powders including a powder of at least one pharmaceutical drug and a powder of a sustained release matrix for the drug. The sustained release matrix consists essentially of non-crystalline, uncrosslinked substituted amylose prepared by reacting, in a basic medium, amylose with at least one organic substituent having a reactive function that reacts with the hydroxy groups of the amylose molecule.

Preferably, the substituted amylose has a substituent to amylose ratio (expressed in mole of substituent per kg of amylose) that is equal to or higher than 0.4. More preferably, such ratio ranges from 0.4 to 7.0.

When the pharmaceutical drug(s) used in the tablet is (are) very slightly soluble, the powder of such drug(s) may represent up to 80% by weight of the tablet.

When, however, the pharmaceutical drug(s) is (are) highly soluble, the powder of such drug(s) should not exceed 40% by weight of the tablet.

The tablet according to the invention can also be of the dry coated type. In such a case, its core will include most of the powder of said drug(s) (for example, the core could contain 95% by weight of drug, the balance consisting of a filler or of substituted amylose). The shell will then be made almost exclusively of substituted amylose, in order to achieve the requested controlled release.

Preferably, the organic substituent is selected from the group consisting of epoxy alkanes, epoxy alcohols, epoxy ethers, epoxy aryls, cycloalkene oxides, halogeno alkanes, halogeno alcohols, alkyl and aryl isocyanates and phosphorus oxychloride.

For the purpose of simplicity, the substituted amylose prepared and used in accordance with the invention will be hereinafter referred as SA, X-n, where SA is the acronym of substituted amylose, X is a code defining the substitute used (G for glycidol; B for 1,2-epoxybutane; C for 1-chlorobutane and D for 1,2-epoxydodecane) and n represents the degree of substitution expressed as the ratio of mole of substituent per kilogram of amylose. For example, SA, G-1.1 will mean that amylose was substituted with glycidol in a proportion of 1.1 mole of glycidol per Kg of amylose.

The invention and its advantages will be better understood upon reading the following non-restrictive detailed description and examples, reference being made to the accompanying drawings.

DETAILED DESCRIPTION OF THE INVENTION

Preliminary considerations

Starch is the major component of the diet in human populations. It is also the major storage carbohydrate of all higher plants. In the plant reserve organs, starch is deposited in the form of granules having a size that ranges between 1 and 100 microns.

Figure 1A:
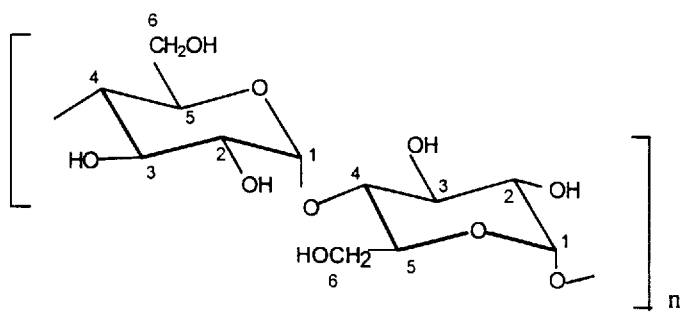
FIGS. 1a and 1b are 3-D and 2-D representations of the chemical structure of amylose, respectively.
Figure 1B:
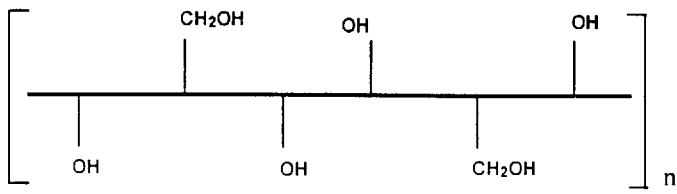
Figure 2A:
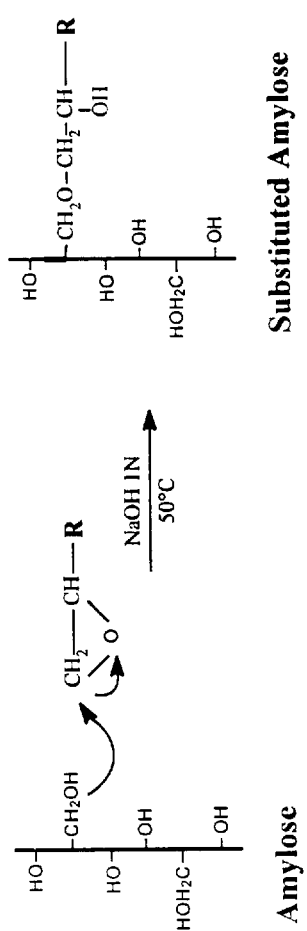
FIG. 2 is a representation of the different steps of the synthesis of substituted amylose.
Figure 2B:
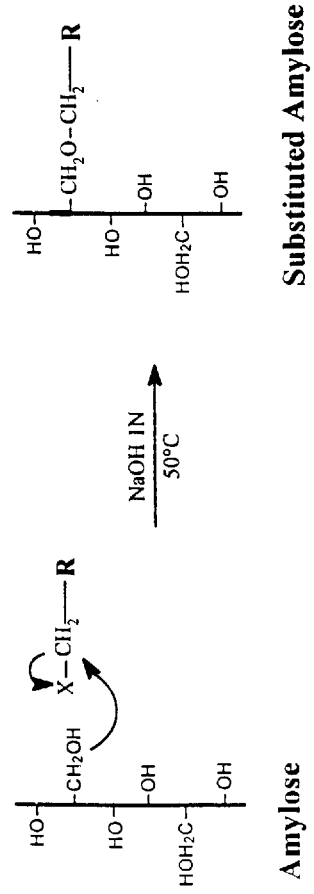
Figure 2C:
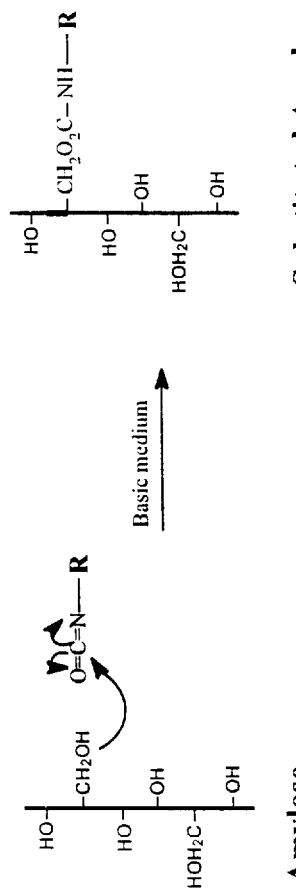
Figure 2D:
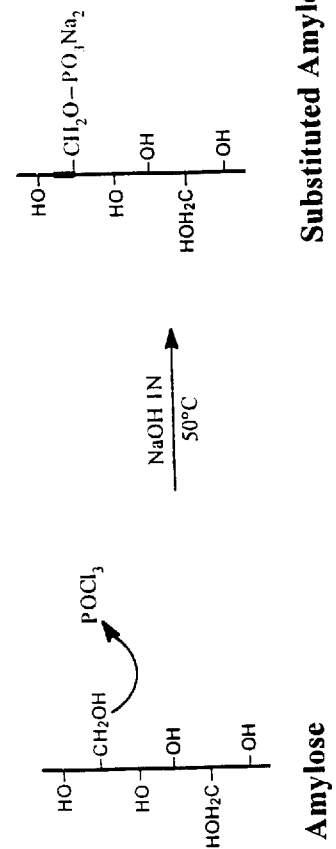
Figure 3:
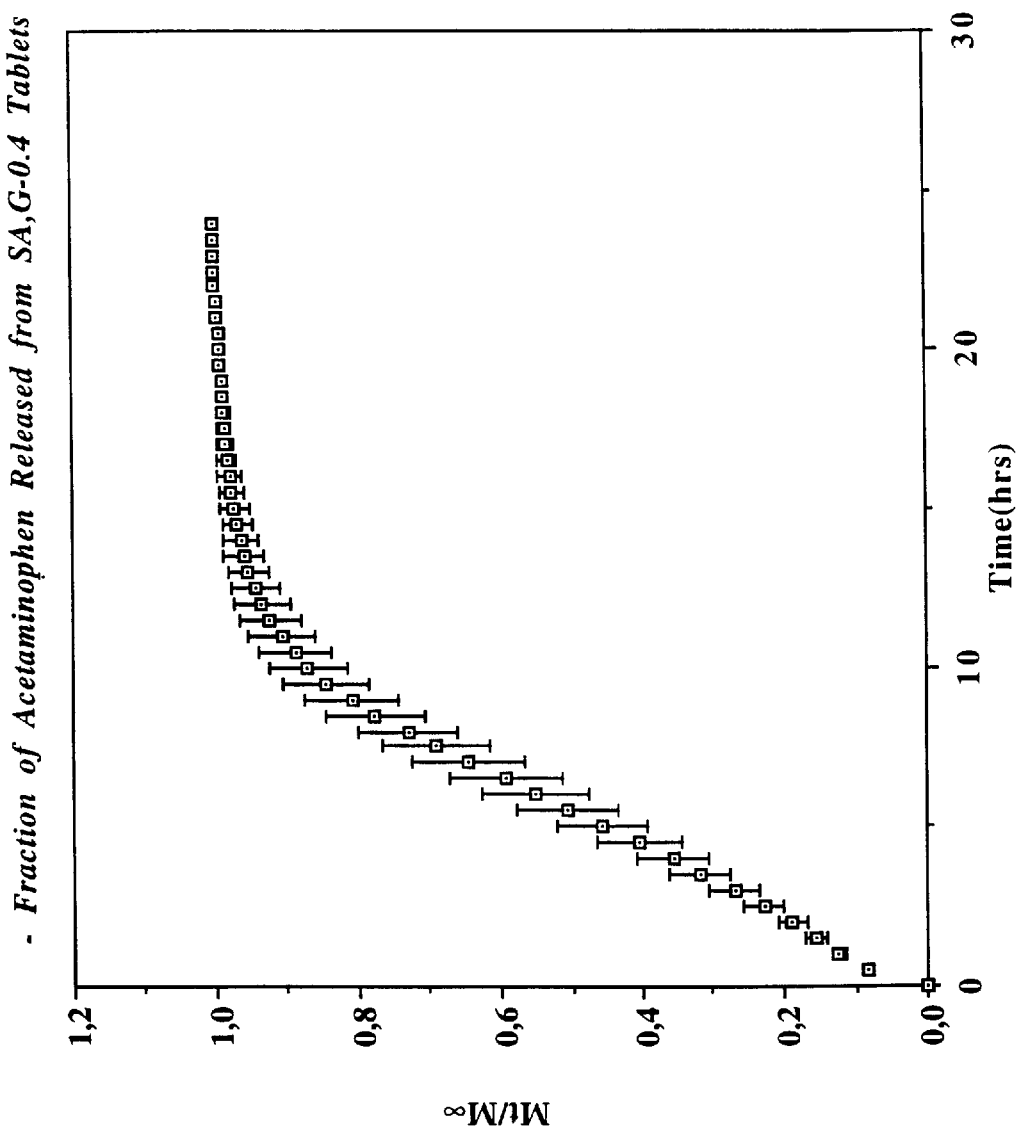
FIG. 3 is a diagram giving the fraction of acetaminophen released from SA,G-0.4 tablets containing the same, as a function of the time.
Figure 4:
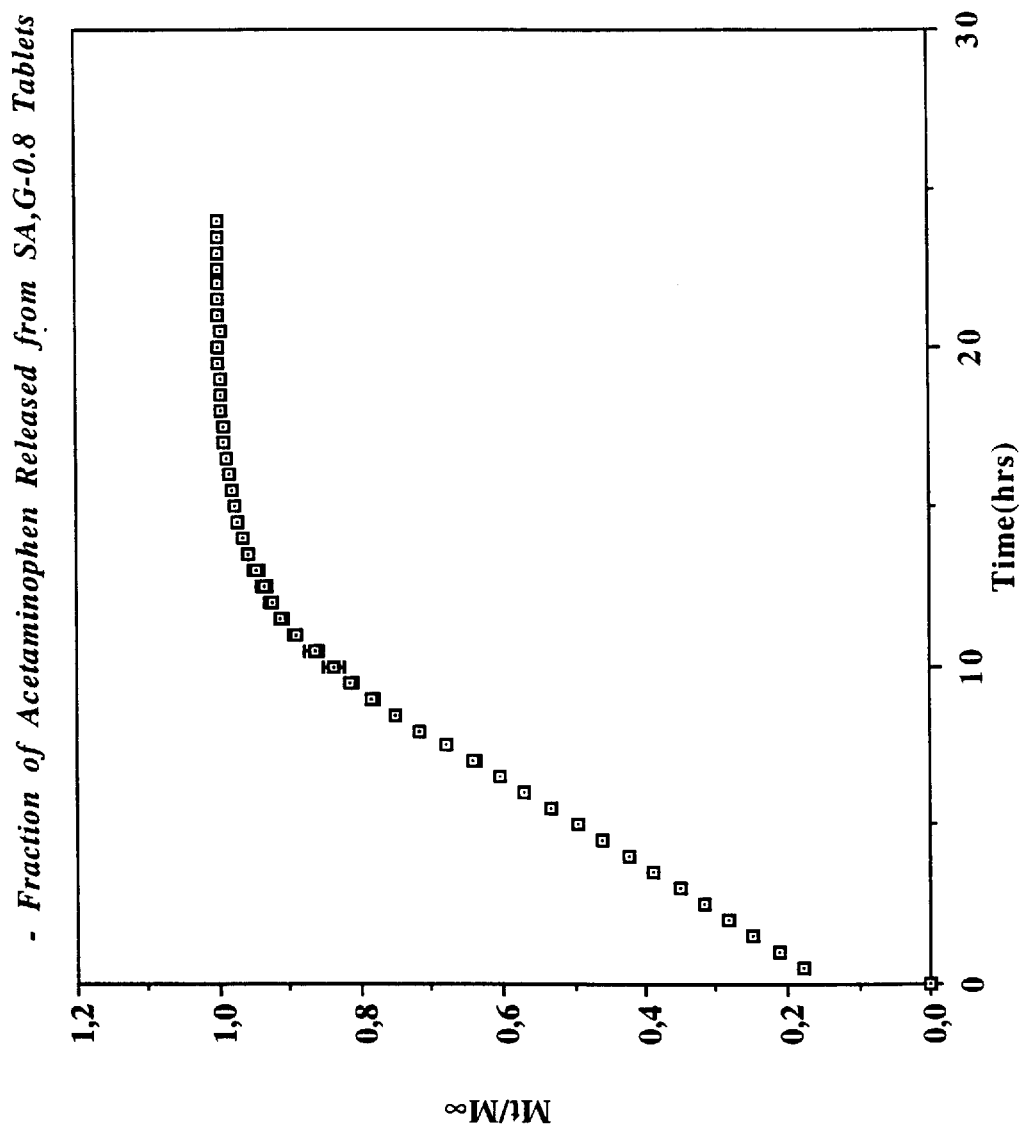
FIG. 4 is a diagram giving the fraction of acetaminophen released from SA,-G-0.8 tablets, as a function of the time.
Figure 5:
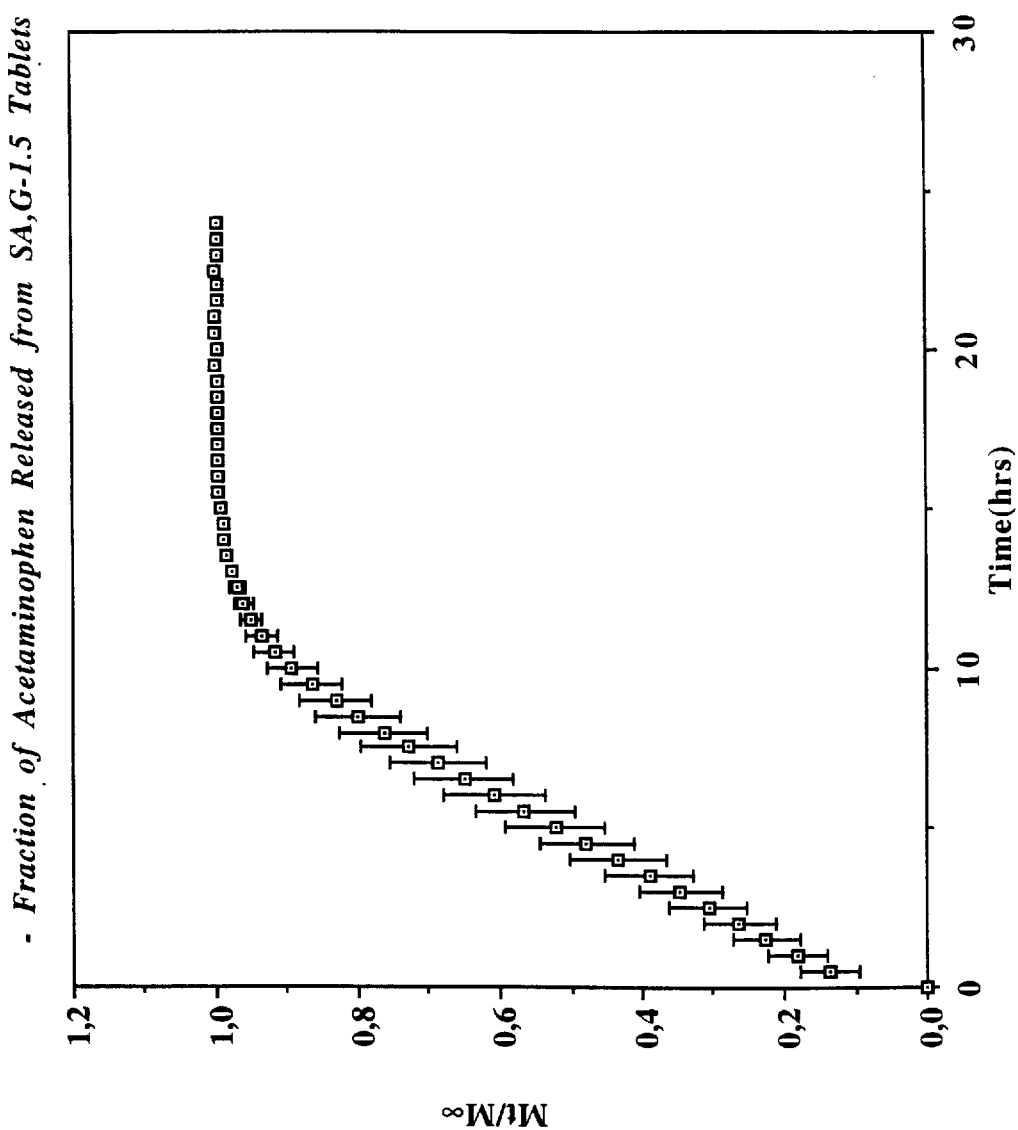
FIG. 5 is a diagram giving the fraction of acetaminophen released from SA,G-1.5 tablets, as a function of the time.
Figure 6:
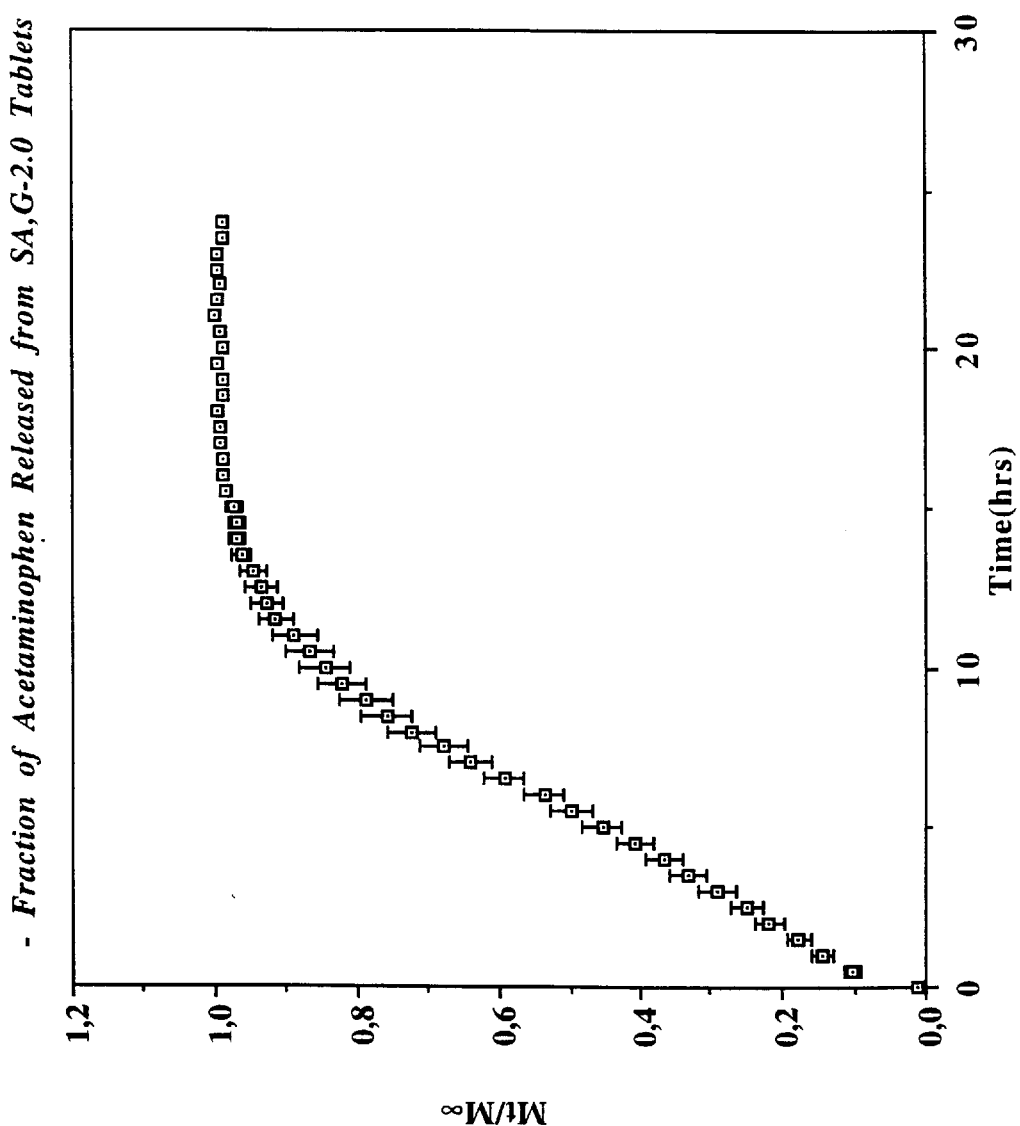
FIG. 6 is a diagram giving the fraction of acetaminophen released from SA,G-2.0 tablets, as a function of the time.

Starch granules present a macromolecular heterogeneity. Indeed, as was already explained hereinabove, starch can be fractionated into two polydisperse polyglucan components. The first one is amylose which is an essentially linear polymer of glucopyranose units linked through α-D-(1,4) linkages (see FIGS. 1a and b). The second component is amylopectin which is a highly branched polymer containing short chains linked to the C-6-hydroxymethyl position of certain glucose moieties, via α-D-(1,6) linkages. Amylose, which is the linear polymer component, contains about 4,000 glucose units. In contrast, amylopectin, which is the branched polymer component, contains about 100,000 glucose units.

Hence, amylose and amylopectin differ not only in their chemical structures but also in their digestibility susceptibility, their stability in dilute aqueous solutions, their gel texture and their film properties.

In the case of amylose, the linkage between the groups is specified in the ordinary way: α-Glc-(1→4)-α-(Glc)n-(1→4)-Glc. The preferred conformation of amylose is an helix of variable dimensions, usually left-handed, with an open-core. The consequence is that the hydroxy group located on C-6 is the most reactive followed by hydroxy groups on C-3 and finally C-2 (see FIG. 1a). Thus, it is possible to use a substituent and chemically modify these OH groups by, for example, an etherification process, thereby leading to substituted amylose.

Substituted amylose synthesis

Substituted amylose (SA) synthesis is outlined in FIG. 2. As can be seen, SA is prepared by reacting amylose with a substituent, typically 1,2-epoxypropanol, in a strongly basic medium.

The substituent that can be used, can be represented by the following formula:

A—R wherein A represents an epoxy function, a halide, or any other suitable organic function such as an isocyanate or phosphate group which is able to react with the hydroxy groups located in position 2, 3 and/or 6 on the amylose molecule, and R represents an organic radical.

One of the preferred substituted amyloses is obtained by using 1,2-epoxypropanol (glycidol) as substituent. However, interesting polymers can also be obtained with other substituents. In such cases, the controlled release properties will depend on the length of the chain R, the steric hindrance due to R, the presence of hydroxy groups on R or resulting from the reaction of the epoxy function, the presence of ionisable functions (—COOH, for example) and/or the hydrophobicity of R. A list of possible substituents is given in Table 1. However, this list is not exhaustive and just given to illustrate the invention.

TABLE 1

LIST OF RADICALS THAT CAN BE GRAFTED

1. Substitution through an epoxy function (A = CH₂—CH—)
                                              \\_O_/

1.1. Epoxy alkane

| | |
|---|---|
| R = —CH₂CH₃ | 1,2-epoxybutane |
| R = —(CH₂)₅CH₂CH₃ | 1,2-epoxydecane |
| R = —(CH₂)₅CH₂CH₃ | 1,2-epoxydodecane |

1.2. Eyoxy alcohol

| | |
|---|---|
| R = —CH₂OH | glycidol (1,2-epoxypropanol) |
| R = —(CH₃)CH₂OH | glycidol methyl |

1.3. Epoxy ether

| | |
|---|---|
| R = —CH₂OCH₂CH₂CH₂CH₃ | butyl glycidyl ether |
| R = —CH₂OC(CH₃)₃ | tert-butyl glycidyl ether |
| R = —CH₂OCH(CH₃)₂ | glycidyl isopropyl ether |
| R = —CH₂OC(O)CH₃CH₂CH₃ | glycidyl butyrate |

1.4. Epoxy aryls

| | |
|---|---|
| | 2,3-(epoxypropyl) benzene |

TABLE 1-continued

LIST OF RADICALS THAT CAN BE GRAFTED

| | |
|---|---|
| | 1,2-epoxy-3-phenoxypropane |
| | glycidyl 4-methoxyphenyl ether |

1.5. Cycloalkene oxide

| | |
|---|---|
| | cyclopentene oxide |
| | cyclohexene oxide |
| | cyclooctene oxide |

2. Substitution through a halide (A = halogen)

2.1. Bromo radicals (A = Br)
2.1.1. Bromo alkane

| | |
|---|---|
| R = —CH₂CH₃ | bromoethane |
| R = —(CH₂)₂CH₃ | 1-bromopropane |
| R = —(CH₂)₃CH₃ | 1-bromobutane |
| R = —(CH₂)₅CH₃ | 1-bromohexane |
| R = —(CH₂)₆CH₃ | 1-bromoheptane |
| R = —(CH₂)₁₁CH₃ | 1-bromododecane |

2.1.2. Bromo alcohol

| | |
|---|---|
| R = —CH₂CH₂OH | 2-bromo ethanol |
| R = —(CH₂)₂CH₂OH | 3-bromo-1-propanol |
| R = —CH₂—CH(OH)—CH₂OH | 3-bromo-1,2-propanediol |
| R = —CH₂(OH)CH₃ | 1-bromo-2-propanol |
| R = —(CH₂)₅CH₂OH | 6-bromo-1-hexanol |
| R = —(CH₂)₆CH₂OH | 7-bromo-1-heptanol |
| R = —(CH₂)₉CH₂OH | 10-bromo-1-decanol |
| R = —(CH₂)₁₁CH₂OH | 12-bromo-1-dodecanol |

2.2. Chloro radicals (A = Cl)
2.2.1. Chloro alkane

| | |
|---|---|
| R = —(CH₂)₂CH₃ | 1-chloropropane |
| R = —(CH₂)₃CH₃ | 1-chlorobutane |
| R = —(CH₂)₅CH₃ | 1-chlorohexane |
| R = —(CH₂)₆CH₃ | 1-chloroheptane |

2.2.2. Chloro alcohol

| | |
|---|---|
| R = —CH₂CH₂OH | 2-chloro ethanol |
| R = —(CH₂)₂CH₂OH | 3-chloro-1-propanol |
| R = —CH₂—CH(OH)—CH₂OH | 3-chloro-1,2-propanediol |
| R = —CH₂(OH)CH₃ | 1-chloro-2-propanol |
| R = —(CH₂)₃CH₂OH | 4-chloro-1-butanol |
| R = —(CH₂)₅CH₂OH | 6-chloro-1-hexanol |

2.3. Iodo radicals (X = 1)
2.3.1. Iodo alkane

| | |
|---|---|
| R = —CH₂CH₃ | iodoethane |
| R = —(CH₂)₃CH₃ | 1-iodobutane |
| R = —CH₂(CH₃)CH₂CH₃ | 2-iodobutane |
| R = —(CH₂)₁₁CH₃ | 1-iodododecane |

2.3.2. Iodo alcohol

| | |
|---|---|
| R = —CH₂CH₂OH | 2-iodo ethanol |

As aforesaid, substitution can also be achieved through an isocyanate group (A being —N=C=O). Therefore, isocyanate containing, substituent can be useful derivatives for coupling a radical R to the hydroxyl group of amylose chains through a stable urethane linkage. The reaction can be carried out in an organic solvent with triethylamine as a basic catalyst or in an aqueous basic medium, as follows:

[Amylose]—OH+R—N=C=O→[Amylose]—O₂C NH—R

Substitution can further be achieved by using phosphorus oxychloride to prepare phosphorylated amylose. In such case, phosphate groups are attached to the amylose chain through the hydroxyl groups of the same by allowing phosphorus oxychloride to react with alkaline amylose, as follows.

[Amylose]—ONa+POCl₃+4 NaOH→[Amylose]—O—PO₃Na₃+3 NaCl+2 H₂O

To prepare the requested substituted amylose, amylose is swollen in an alkaline medium such as NaOH (1N), heated to 50° C. After homogenization, a desired quantity of substituent is added gradually. After complete homogenization, a SA gel is obtained, which is then neutralized. Distilled water heated to 50° C. is added, followed by a sufficient amount of acetic anhydride to get a pH of 7.0. Then, a 85% v/v acetone/water solution is added to the obtained gel and the content is then washed through a Büchner funnel. Recovered gel is washed twice with 40% acetone/water and finally three times more with 100% acetone. The resulting solid is exposed overnight to air.

The degree of substitution can be adjusted varying the substituent to amylose ratio (mole of substituent per kg of amylose). Hence, different degrees of substitution were, for example, obtained with glycidol, ranging from 0.1 to 10.0.

Use of substituted amylose as a matrix for sustained drug release

As aforesaid, substituted amylose is a very interesting excipient for the preparation of drug controlled release tablets. Advantages include a very easy synthesis of the polymer, an easy manufacturing of tablets by direct compression, the possibility of a large range of drug concentration in the tablet, the versatility of the matrix, which is hydrophilic, good mechanical properties of tablets obtained by direct compression and safety of substituted amylose.

The pharmaceutical sustained release tablets according to the invention can be prepared by compressing, as is known per se, a blend of at least two dry powders including a pharmaceutical drug powder in an amount of up to 80% by weight of the whole tablet, and a powder of substituted amylose used as sustained release matrix. If desired, the tablets may also include a small amount of a lubricant, and one or more fillers also in a powder form. If desired, a mixture of two or more drugs may be used instead of one.

The method of preparing such tablets is well known in the art and needs not be described further.

The pharmaceutical sustained release tablets according to the invention can also be of the dry-coated type. In such case, the amount of drug may represent up to 75% by weight of the total weight of the tablets, if the drug is poorly soluble. If it is very soluble, the amount of drug may represent up to 55% by weight of the total weight of the tablets. The dry coated tablets according to the invention can also be prepared by direct compression. First, the core of the tablet can be prepared by compressing a mixture of the drug with a very low amount of the polymer. Secondly, the core can be placed on a substituted amylose powder bed in a die and recovered by the same. This is followed by a compression of the core-shell system.

Once again, this method of preparing dry-coated tablet is well known and needs not be described further.

Bioadhesion properties

Experiments carried out by the Applicant on SA, G-n tablets have demonstrated strong adhesion to the glass vessel in vitro, for degrees of substitution higher than 4 in the case of glycidol as substituent. Thus such tablets could potentially be used as bioadhesive dosage forms.

Possibility of resistance to alpha-amylase and other enzymes

Amylose has been described as sensitive to alpha-amylase. Cross-linked amylose has also been described as sensitive to α-amylase at low degrees of cross-linking. At high degrees of cross-linking, cross-linked amylose is not useful for controlled release since it acts as a disintegrant.

Some experiments made by the Applicant have demonstrated that by choosing carefully the substituting agent and the degree of substitution, it is possible to protect the amylose from degradation and evermore to modulate the rate of enzymatic degradation of the polymer. This opens the door to a very interesting field of research and development, with promising commercial applications.

For example, it has already been demonstrated that by choosing carefully the substituting agent and the degree of substitution, it is possible to protect the amylose from degradation of evermore to modulate the rate of enzymatic degradation of the polymer.

For example, it has already been demonstrated that substitution through epoxy-dodecane creates a steric hindrance and a hydrophobic environment protecting the polymer against enzymatic degradation.

However, it could also be assumed that a high degree of substitution could hinder the penetration of the enzyme inside the tablet by the high viscosity of the polymer.

Grafting of substituting agents containing carboxylic groups (A—R— COOH) could also be useful, as the carboxylic groups would be able to react with Ca++, thereby inhibiting the alpha-amylase which needs these ions to be active.

EXAMPLE 1

Substitution of amylose with glycidol (1,2-epoxypropanol)

300 g of amylose (Hylon® VII, National Starch and Chemical Company) were added to 1.8 l of NaOH 1N heated to 50° C. The mixture was homogenized for 15 minutes in a Hobart planetary mixer, at the first speed.

60 g of glycidol (Sigma Chemical Company, St Louis, USA, batch #84H3455, $C_3H_6O_2$, FW=74.08, d=1.117 g/ml) were added gradually and homogenization was continued for another 15 minutes at the same speed.

The obtained gel was neutralized. First 1.5 l of distilled water heated to 50° C. was added, followed by the necessary volume of acetic anhydride in order to get a pH of 7.0. Homogenization was continued for another 5 minutes at the same speed.

The obtained gel was transferred equally into two separate 4 liters beakers. 2 Liters of a 85% acetone/water solution were added to each one and stirred manually. The content of each beaker was then washed through a Büchner funnel. The gel recovered from both beakers was washed twice with a mixture of 40% acetone/water and finally three times more with 100% acetone. The resulting powder was exposed overnight to air.

As aforesaid, the product prepared according to this example will be referred to hereinafter as SA,G-2.7 (Substituted Amylose, prepared with Glycidol and having a degree of substitution of 2.7 moles of glycidol per kg of amylose).

EXAMPLE 2

Substitution of amylose with glycidol with different degrees of substitution

By proceeding in the same manner as in Example 1, SA,G having other degrees of substitution were obtained by simply varying the glycidol/amylose ratio. This ratio may be expressed in mole of Glycidol/per kg of amylose and will be defined as the degree of substitution.

The SA,G that were so obtained will be hereinafter identified as SA,G-0.1, 0.4, 0.8, 1.1, 1.5, 2.0, 2.7, 3.4, 4.0, 5.4, 7.0 and 10.0. Table 2 shows the relative amounts of amylose and glycidol that were used to obtain the aforesaid degrees of substitution.

TABLE 2

| Amylose (g) | Glycidol (g) | Glycidol/Amylose (mol/Kg) |
|---|---|---|
| 300 | 2.25 | 0.1 |
| 300 | 9 | 0.4 |
| 300 | 18 | 0.8 |
| 300 | 24 | 1.1 |
| 300 | 33 | 1.5 |
| 300 | 45 | 2.0 |
| 300 | 60 | 2.7 |
| 300 | 75 | 3.4 |
| 300 | 90 | 4.0 |
| 300 | 120 | 5.4 |
| 300 | 157.5 | 7.0 |
| 300 | 225 | 10.0 |

EXAMPLE 3

Effect of the degree of substitution of the polymer on the in vitro Tablet Release Profile (a) preparation of the tablets In order to illustrate the advantages of the present invention, acetaminophen was selected as model for a release profile study. Batches of tablets were prepared with the different substituted amylose polymers listed in Table 2, and with acetaminophen as drug with a drug percentage of 10% by weight.

The drug and the substituted amylose SA,G-2.7 were mixed manually in a mortar. Tablets weighing 400 mg each were compressed at a 2.5 ton/cm² pressure on an IR 30-tons press (C-30 Research & Industrial Instruments Company, London, U.K.). The diameter of the tablets was 1.26 cm.

The same procedure was applied with all the polymers listed in Table 2. Consequently, tablets containing SA,G-0.4, 0.8, 1.5, 2.0, 3.4, 4.0, 5.4 or 7.0 with 10% of acetaminophen were also prepared.

(b) In vitro drug release from the tablets

Tablets prepared as disclosed hereinabove in paragraph (a), were placed individually in 900 ml of a phosphate buffer solution medium, (pH=7.34), at 37° C., in an U.S.P. XX dissolution apparatus equipped with a rotating paddle (50 rpm). The drug release was followed spectrophotometrically (acetaminophen: 242 nm) and continuously recorded. The drug release results were expressed using the equation proposed by Peppas [Lenaerts V. et al., J. Controlled Rel. 15, 39–46 (1991)]

$$M_t/M = kt^n$$

where $M_t$ is the amount released at time t; M is the total amount released; t is the time; k is a kinetic constant and n is a number characterizing the release mechanism.

Thus, each release profile was expressed as a plot of $M_t/M$ as function of the time (t). Each tablet formulation was tested in triplicate.

(c) Results

Figure 12:
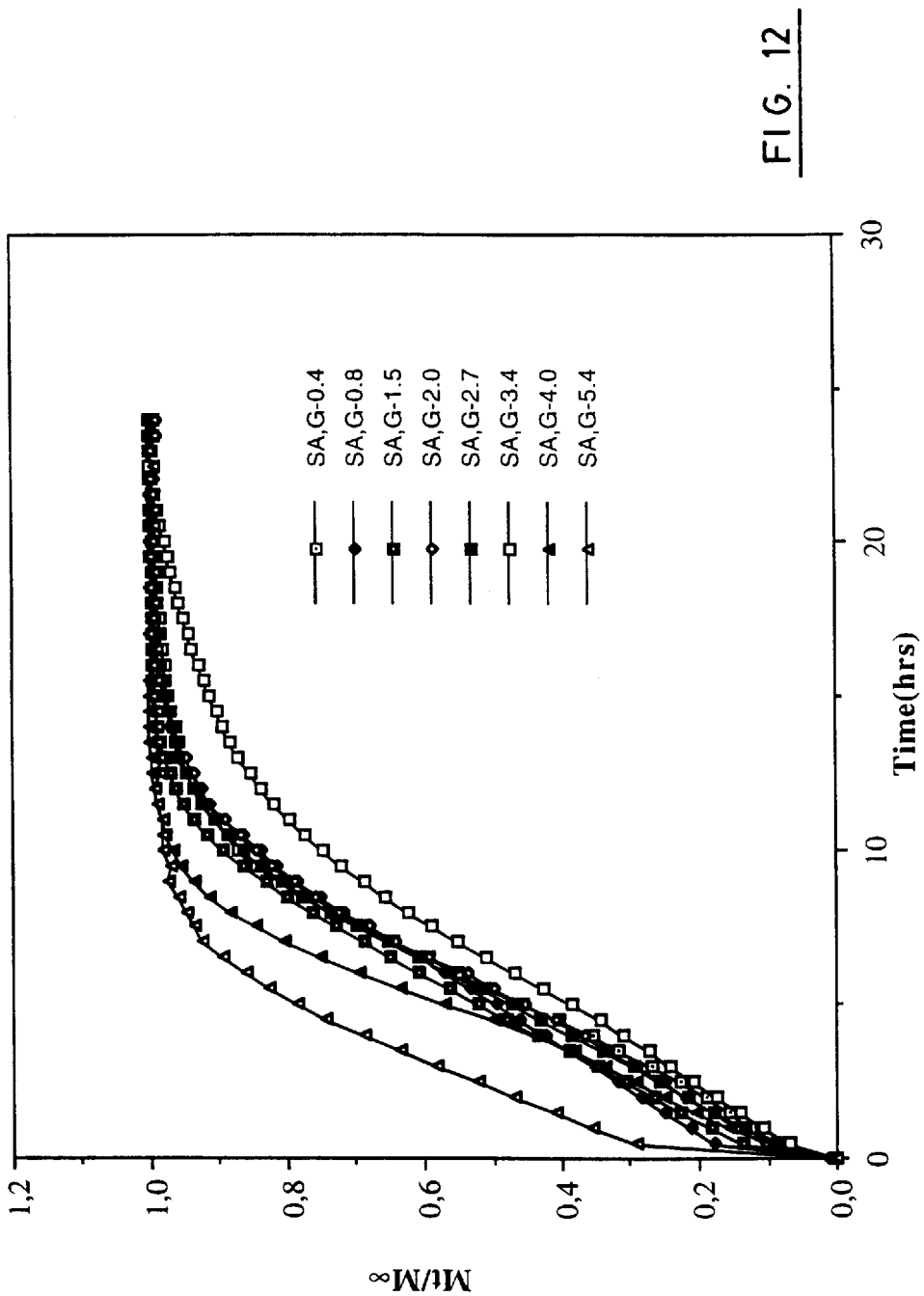
FIG. 12 is a diagram showing the influence of the degree of substitution on the release of acetaminophen released from SA,G-n tablets, as a function of time.

The results are presented in FIGS. 3 to 12. FIGS. 3–11 show the release profile obtained for each polymer individually. FIG. 12 gives a general comparison which shows the influence of the degree of substitution on the release profile of acetaminophen from SA,G-n tablets (n being the degree of substitution).

Clearly, all these Figures show a controlled and sustained release of the drug, with a remarkable close-to-linear profile. The release time ranges from 9 to 20 hours for all the degrees of substitution studied. From SA,G-0.4 to SA,G-2.7, one can see that there is no influence of the degree of substitution on the release profile. For higher degrees, one observes first an increase in the release time, followed by a slight decrease in the release time. Globally speaking, one can say that after reaching the value of 0.4 the degree of substitution has no or little influence on the drug release profile. It is worth noting also that in all the experiments with an acetaminophen percentage of 10%, the tablets remained intact. However, the tablets containing substituted amylose with a low degrees of substitution (0.4 to 1.5) showed a slight lamination, without major effect on the drug release rate.

EXAMPLE 4

Effect of the tablet drug loading on the in vitro tablet release profile (a) preparation of the tablets In order to study the effect of the tablet drug loading on the in vitro tablet release profile, acetaminophen was selected as model for a release profile study. Batches of tablets were prepared with the substituted amylose polymer SA,G-2.7 and with acetaminophen as drug, with a drug percentage ranging from 1 to 40% by weight.

The drug and the substituted amylose SA,G-2.7 were mixed manually in a mortar. Tablets weighing 400 mg each were compressed at a 2.5 tons/cm² pressure on an IR 30-tons press (C-30) Research & Industrial Instruments Company, London, U.K.). The diameter of the tablets was 1.26 cm.

The same procedure was applied with different amounts of acetaminophen in the tablets. Tablets containing 1.0, 5.0, 10.0, 20.0, 30.0 and 40.0% w/w of acetaminophen were so prepared.

(b) in vitro drug release from tablets

Tablets prepared as disclosed in paragraph (a) were placed individually in 900 ml of a phosphate buffer solution medium, pH=7.34, at 37° C., in an U.S.P. XX dissolution apparatus equipped with a rotating paddle (50 rpm). The drug release was followed spectrophotometrically (acetaminophen: 242 nm) and continuously recorded. The drug release results were expressed using the same equation as given hereinabove in Example 3 (b).

Each release profile was expressed as a plot of $M_t/M$ as a function of the time (t). Each tablet formulation was tested in triplicate.

Figure 13:
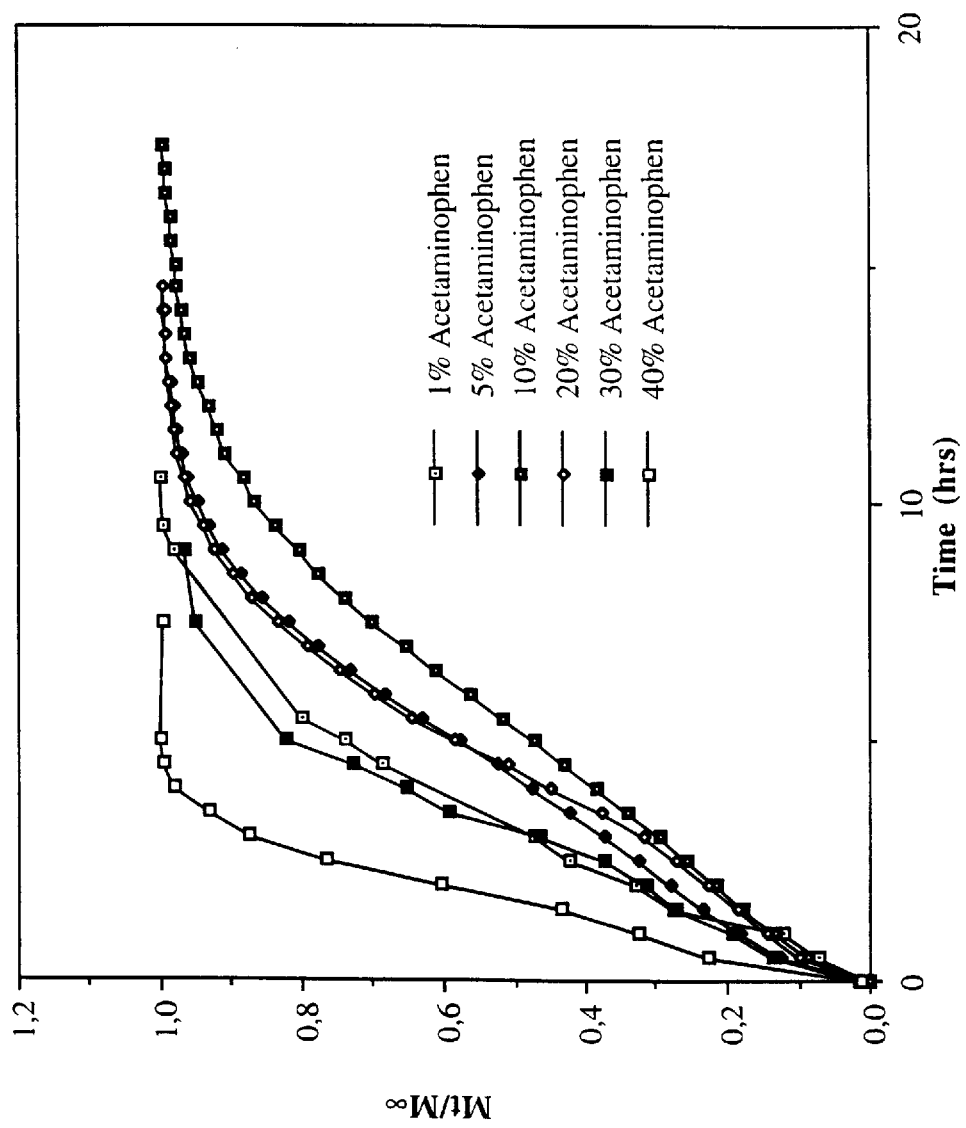
FIG. 13 is a diagram showing the effect of drug loading on the fraction of the acetaminophen released from SA,G-2.7 tablets, as a function of time.
Figure 14:
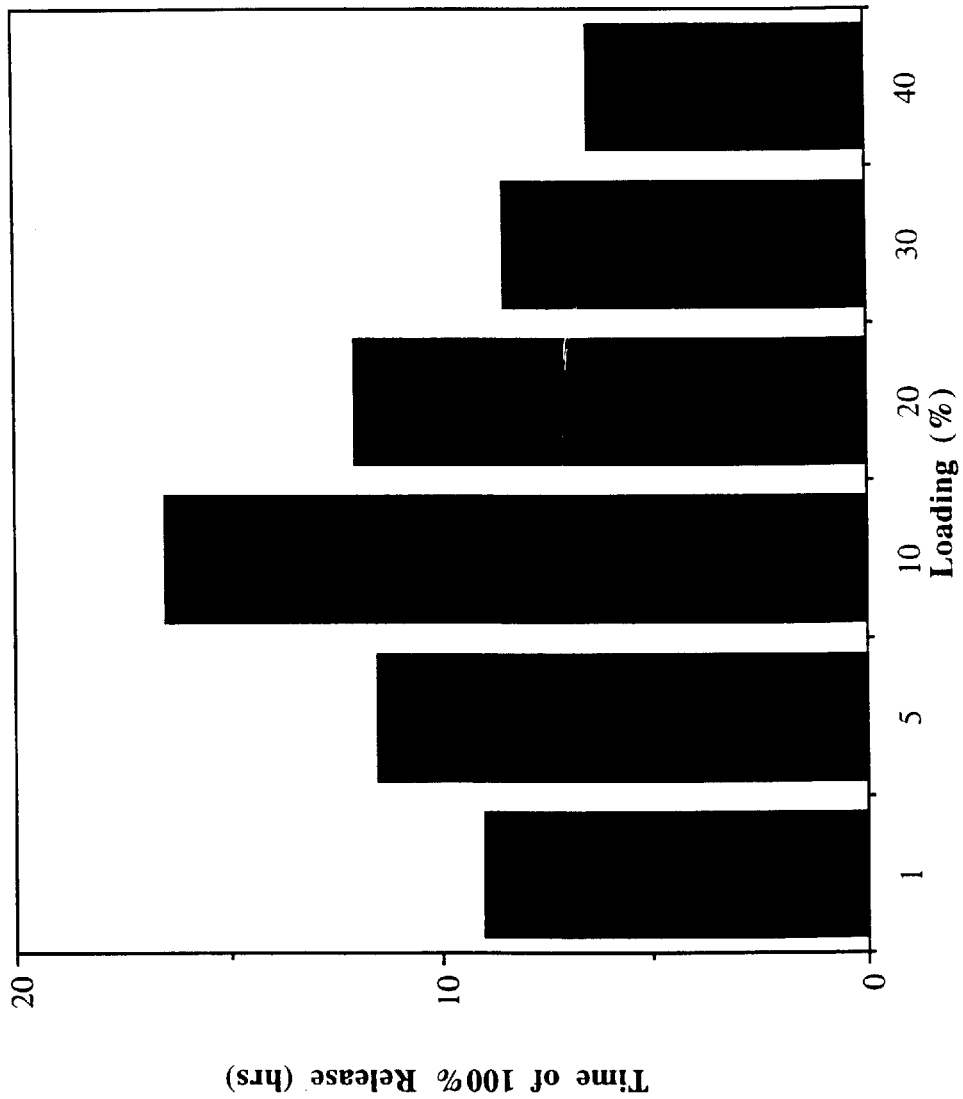
FIG. 14 is a diagram showing the effect of drug loading on the time of 100% acetaminophen released from SA,G-2.7 tablets.

The results are presented in FIGS. 13 and 14. A characteristic pattern is observed in FIG. 14, demonstrating a maximum release time for concentration of 10% of drug. However, there is a clear control of the drug release for concentrations ranging from 1 to 40% of acetaminophen, confirming the excellent potential of this drug delivery system.

This could be explained in the following way. It is believed that substituted amylose controls the drug release by two mechanisms at low drug concentrations, and by three mechanisms at high drug concentrations. In the case of low drug concentrations, the release is controlled by a physically controlled association between the linear chains of the substituted amylose, and by the viscosity of the gel. Both phenomena occur in the presence of water and delay the release of the drug, by hindering the drug diffusion inside the matrix. The swelling results presented in Example 6 hereinabove will confirm this theory. When the drug concentration increases, some erosion appears which competes with the above mentioned mechanisms and accelerates the release process.

13

EXAMPLE 5

Effect on the drug nature on the in vitro tablet release profile

In order to illustrate the versatility and advantages of the present invention, acetaminophen, theophylline and sodium salicylate were selected as models of release profile studies. Batches of tablets were prepared with the substituted amylose polymer SA,G-2.7 and the drug (acetaminophen, theophylline or sodium salicylate), with a drug percentage of 10%.

Acetaminophen (10% w/w) and the substituted amylose SA,G-2.7 were mixed manually in a mortar. Tablets weighing 400 mg each were compressed at a pressure of 2.5 tons/cm$^2$ in an IR 30-tons press (C-30 Research & Industrial Instruments Company, London, U.K.). The diameter of the tablets was 1.26 cm.

The same procedure was applied with different drugs in the tablets. Thus, tablets containing 10.0% w/w of theophylline or sodium salicylate were also prepared.

(b) in vitro drug release from tablets

Tablets prepared as disclosed in paragraph (a) were placed individually in 900 ml of a phosphate buffer solution medium, pH=7.34, at 37° C., in an U.S.P. XX dissolution apparatus equipped with a rotating paddle (50 rpm). The drug release was followed spectrophotometrically (acetaminophen: 242 nm; theophylline: 272 nm; sodium salicylate: 296 nm) and continuously recorded. The drug release results were expressed using the same equation as given in Example 3(b).

Thus, each release profile was expressed as a plot of $M_t/M$ as a function of time (t). Each tablet formulation was tested in triplicate.

(c) results

Figure 7:
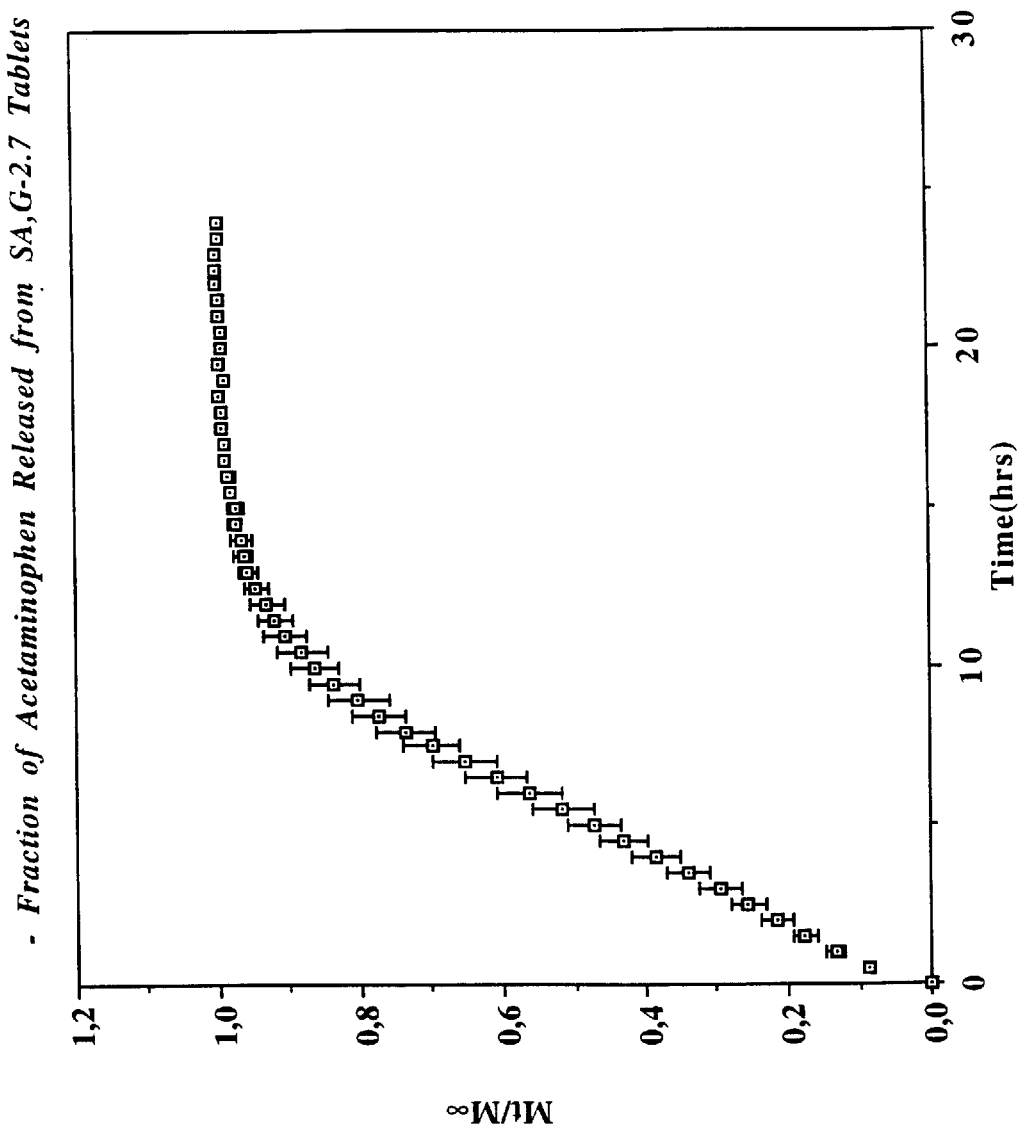
FIG. 7 is a diagram giving the fraction of acetaminophen released from SA,G-2.7 tablets, as a function of the time.
Figure 8:
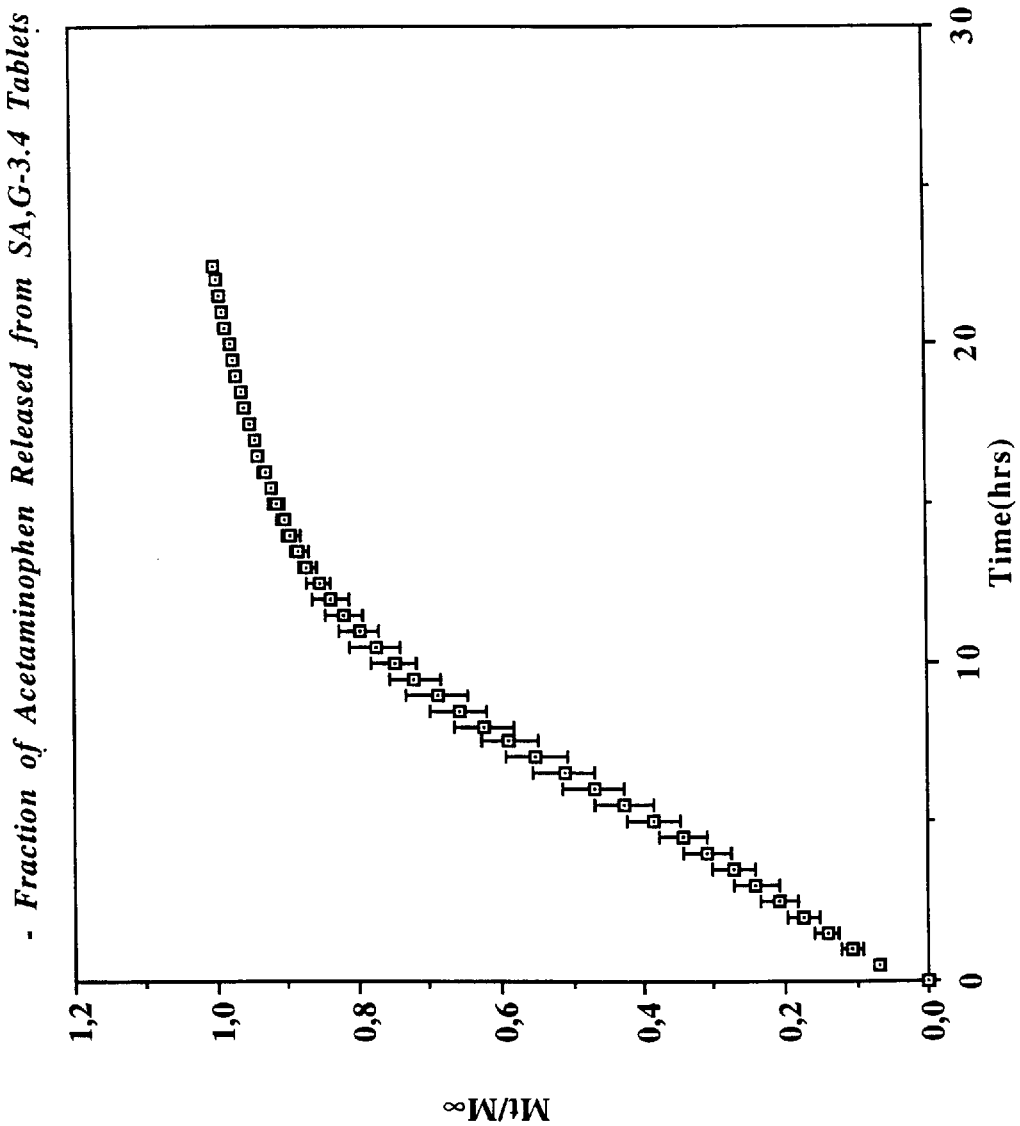
FIG. 8 is a diagram giving the fraction of acetaminophen released from SA,G-3.4 tablets, as a function of the time.
Figure 9:
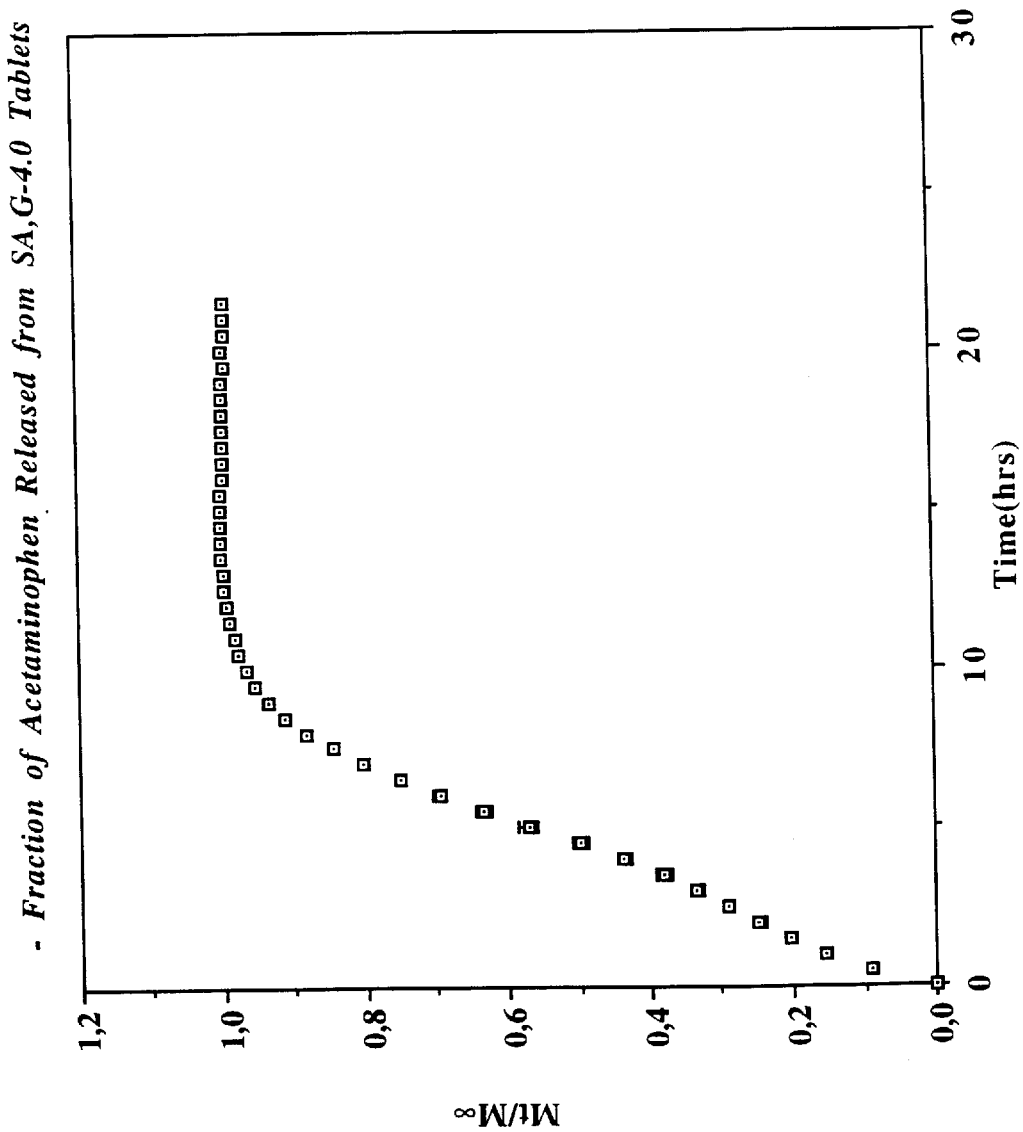
FIG. 9 is a diagram giving the fraction of acetaminophen released from SA,G-4.0 tablets, as a function of the time.
Figure 10:
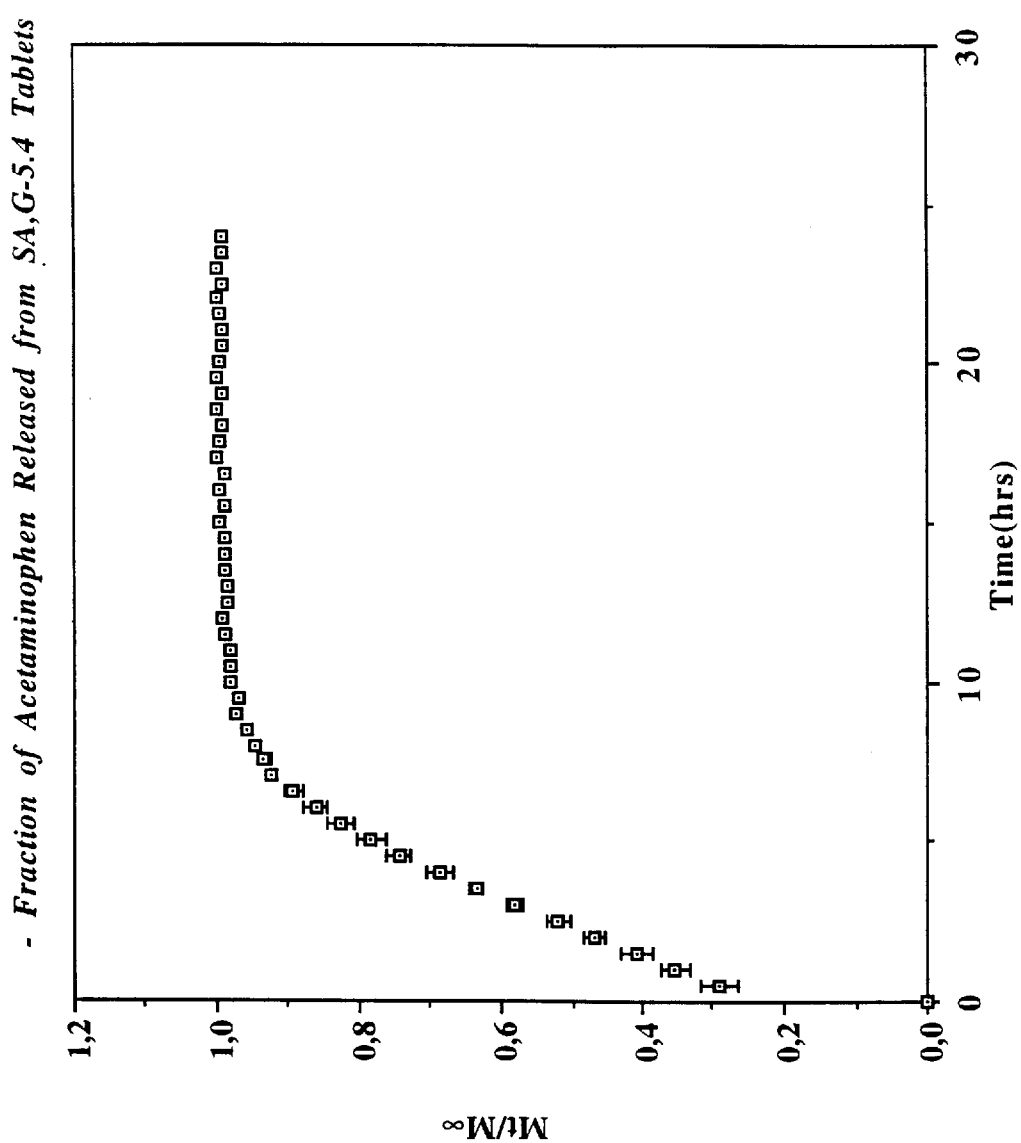
FIG. 10 is a diagram giving the fraction of acetaminophen released from SA,G-5.4 tablets, as a function of the time.
Figure 11:
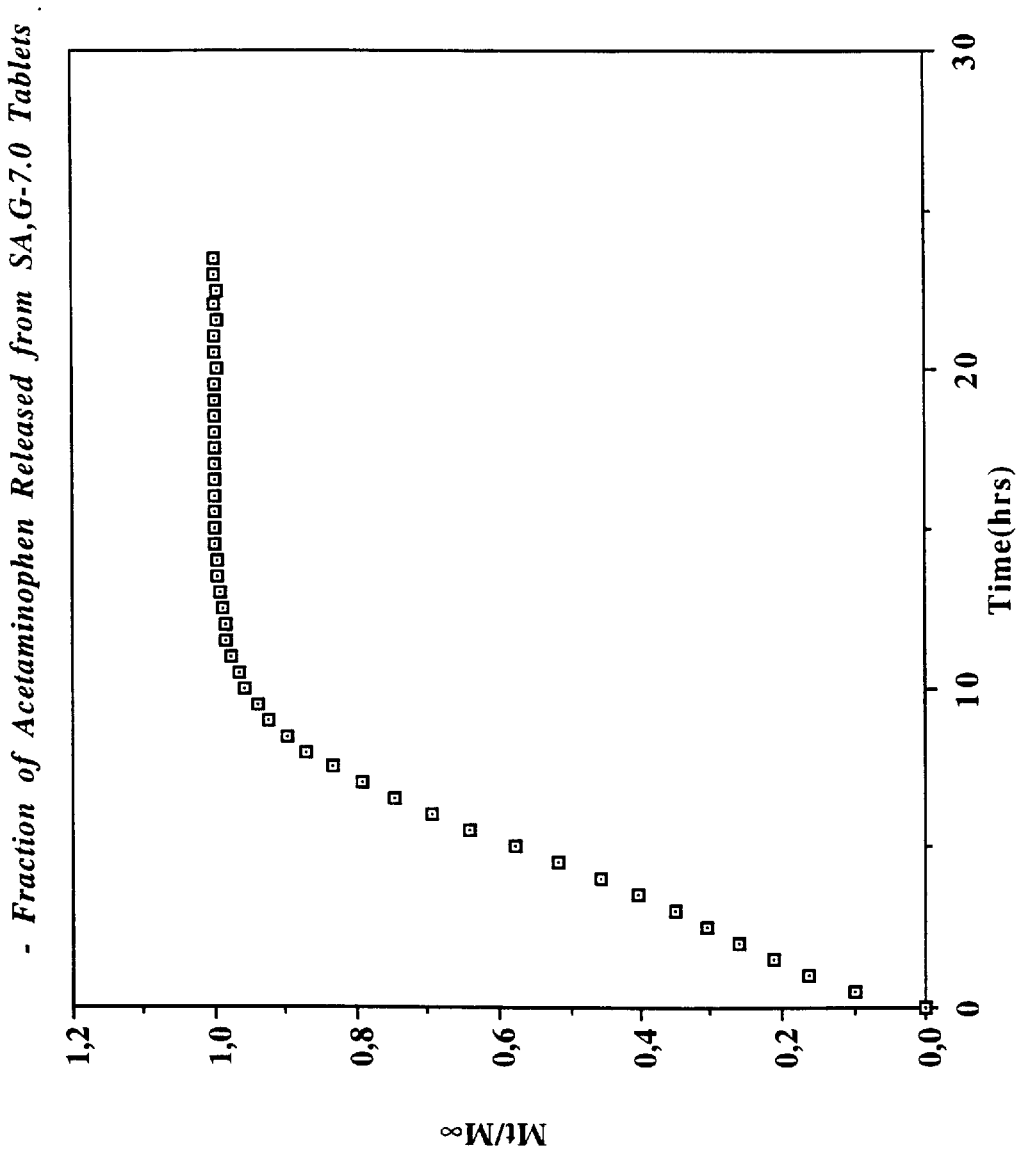
FIG. 11 is a diagram giving the fraction of acetaminophen released from SA,G-7.0 tablets, as a function of the time.
Figure 15:
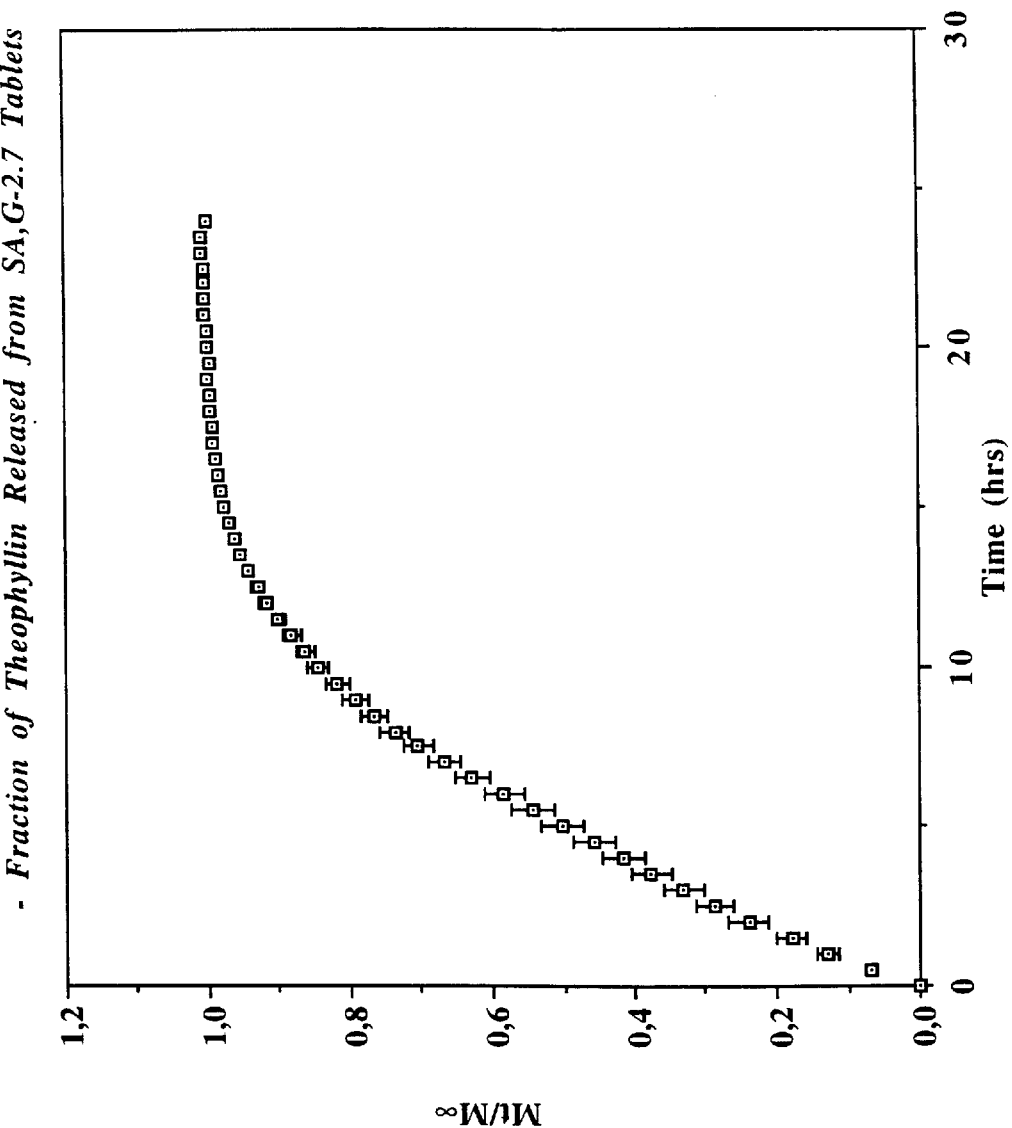
FIG. 15 is a diagram giving the fraction of theophylline released from SA,G-2.7 tablets containing the same, as a function of the time.
Figure 16:
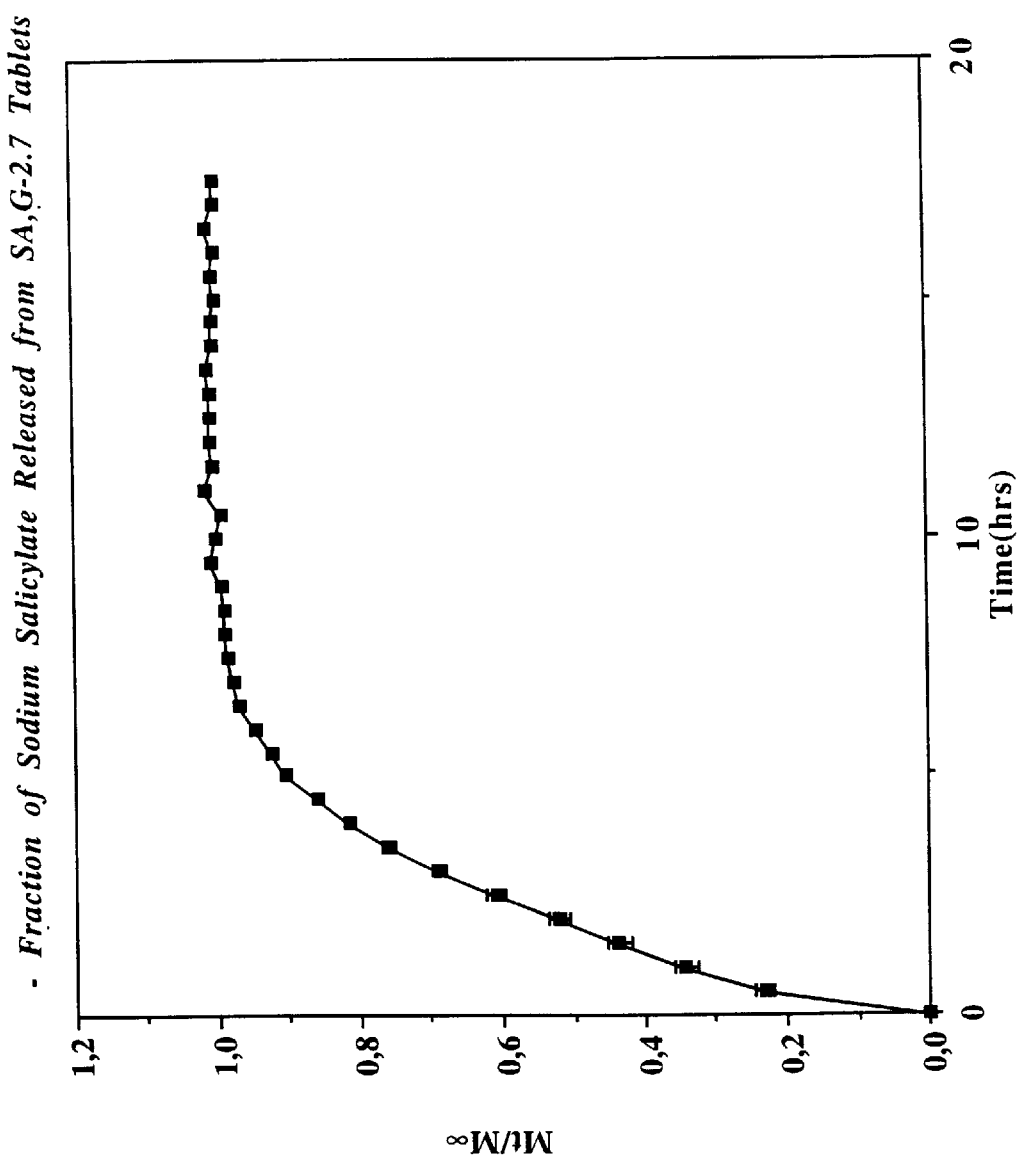
FIG. 16 is a diagram giving the fraction of sodium salicylate released from SA,G-2.7 tablets containing the same, as a function of the time.

The results are presented in FIGS. 7, 15 and 16. It is evident that a controlled and sustained release is obtained for the three drugs, demonstrating the versatility of the system and its commercial potential. Obviously other drugs could be incorporated in the SA tablets of the present invention and would provide similar sustained release characteristics, provided of course these other drugs are in a powder form and thus be processable into a tablet.

EXAMPLE 6

Swelling studies (a) preparation of the tablets

Tablets weighing 400 mg each, compressed on a hydraulic pressed at a 2.5 tons/cm$^2$ pressure were studied. They contained 100% of substituted amylose SA,G-0.4, 0.8, 1.1, 1.5, 2.0, 2.7, 3.4, 4.0, 5.4 and 7.0.

(b) Measurement of water uptake

The swelling behaviour of a polymer can be characterized by measuring its water uptake ability. This measurement helps to understand the mechanism of drug controlled release.

A gravimetric method was used to record the water uptake of the tablets prepared as disclosed in paragraph (a). The measurements were registered in triplicate. At appropriate time intervals, each tablet was removed from the water with forceps, briefly patted with lint-free cleaning tissues to remove the solution wetting its surface, and weighed. New samples were weighed for every time interval. The swelling study was done in distilled water medium pH 6.5, at 37° C.

(c) results

Figure 17:
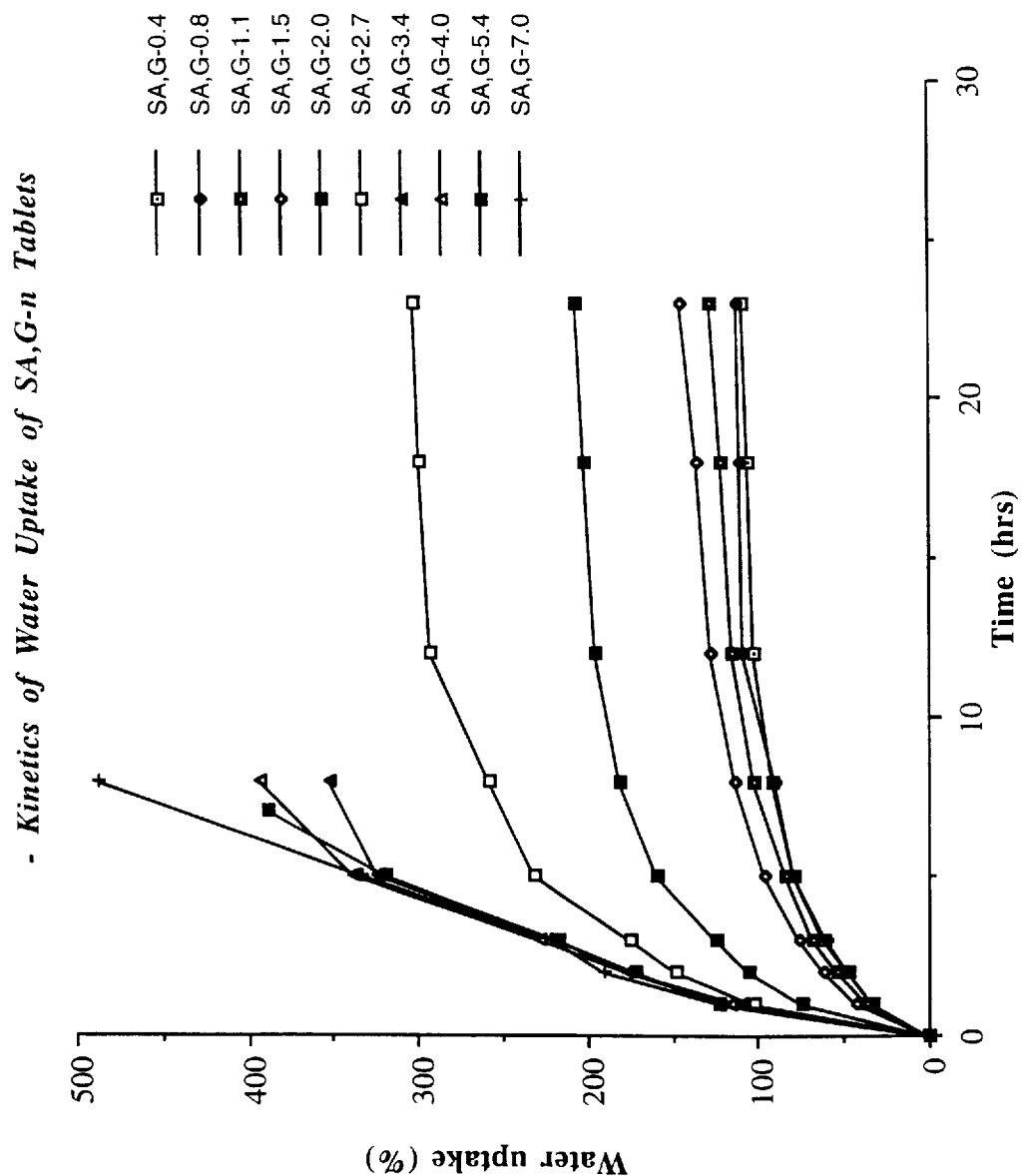
FIG. 17 is a diagram giving the kinetics of water uptake of SA,G-n tablets, as a function of the time.
Figure 18:
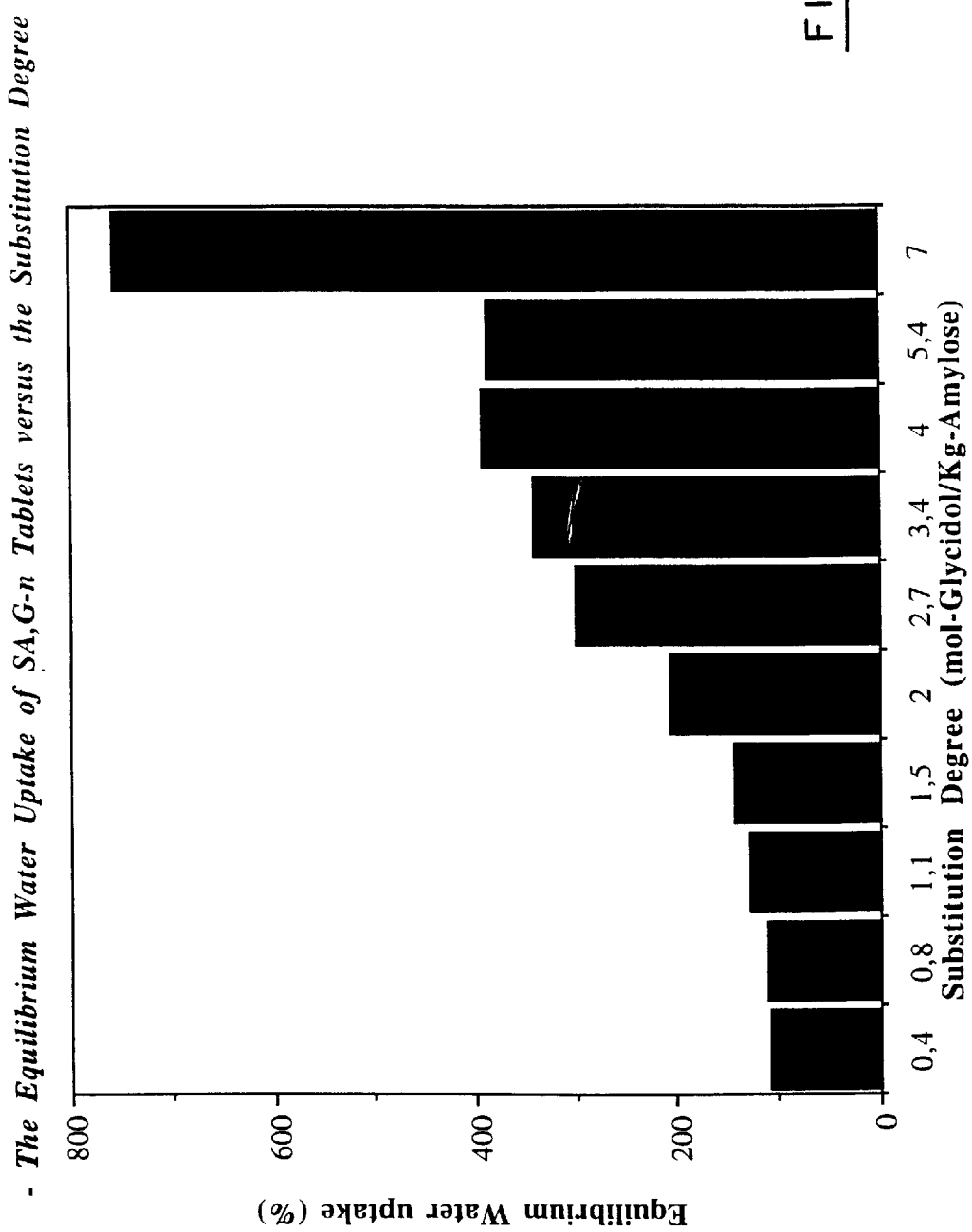
FIG. 18 is a diagram showing the equilibrium water uptake of SA,G-n tablets, as a function of the substitution degree.

The results are expressed as the percentage of water uptake (100×weight of water/weight of tablet) as a function of the time (hours) (see FIG. 17). The equilibrium water uptake was also used to evaluate the influence of the degree of substitution of the polymer on the swelling behaviour of these polymers (see FIG. 18). It must be noted that the equilibrium swelling was not reached in the cases of SA, G-4.0, 5.4 and 7.0, because the tablets could not be removed without damage after 10 hours of immersion. However, it is still possible to observe an increase in water uptake in function of the degree of substitution, even for these high degrees of substitution.

Analysis of the water uptake as a function of the time reveals a significant increase in the amount of water uptake when rising the degree of substitution of the amylose. The adsorbed quantities are high, especially for high degrees of substitution. No desagregation of the tablets was observed for the studied degrees of substitution. Surprisingly, the degree of substitution has no or little effect on the drug release profile, but a major one on the swelling properties. One can cautiously advance that the substitution of the glucose hydroxy groups by glycidol allows the penetration of a larger amount of water. Such, in turn allows a complete gelification of the tablet, thus helping the drug diffusion and release. Increasing the degree of substitution will bring more and more new hydroxy groups coming from the glycidol molecules (see FIG. 2). This will hinder too much the molecular rearrangement process and accelerate the drug release rate. However, this will also favour the water uptake and will create a highly viscous structure which will slow down the drug diffusion. This could explain the two different patterns observed for the swelling and the drug release.

It is worth noting that this particular behaviour is characteristic of this new family of polymers.

EXAMPLE 7

Preparation of tablets for the crushing-strength studies

Different batches of tablets were prepared with the different glycidol substituted amylose polymers described in Table 3, in order to study their binding properties.

All the tablets that were so prepared, contained α-monohydrate lactose 100 mesh as a filler and magnesium stearate as a lubricant. These two products are used on a current basis in the pharmaceutical industry. As is known, α-monohydrate lactose 100 mesh presents poor binding properties. Magnesium stearate is also recognized to decrease crushing-strength of lactose tablets. In spite of the poor binding properties of such lubricant and filler, good results were obtained. This illustrates the unexpected binding properties of substituted amylose.

More specifically, the tablets that were prepared included in their composition:

α-monohydrate lactose 100 mesh (MALLINCKRODT) as a filler;

various concentrations of SA,G-1.1; SA,G-2.0; SA,G-4.0; and magnesium stearate (SIGMA CHEMICAL COMPANY, St. Louis, USA) as a lubricant.

A well known binder, Avicel PH-101® (FMC Corp., Philadelphia, USA) was also used in some tablets in place of substituted amylose for comparison purpose, since this product is one of the best binding agents presently available on the market.

Typically, α-monohydrate lactose 100 mesh, magnesium stearate and substituted amylose were mixed manually in a mortar. Tablets weighing 500 mg each were compressed at a 2 tons/cm$^2$ pressure in an IR 30-tons press (C-30 Research & Industrial Instruments Company, London, U.K.). The diameter of the tablets was 1.26 cm.

TABLE 3

Propositions of ingredients in the tablets
(expressed in % by weight)

| Formulation | SA, G-1.1 | SA, G-2.0 | SA, G-4.0 | Avicel PH 101 | Lactose 100 mesh | Mg st. |
|---|---|---|---|---|---|---|
| 1 | 0 | 0 | 0 | 0 | 99.5 | 0.5 |
| 2 | 10 | 0 | 0 | 0 | 89.5 | 0.5 |
| 3 | 20 | 0 | 0 | 0 | 79.5 | 0.5 |
| 4 | 25 | 0 | 0 | 0 | 74.5 | 0.5 |
| 5 | 0 | 10 | 0 | 0 | 89.5 | 0.5 |
| 6 | 0 | 20 | 0 | 0 | 79.5 | 0.5 |
| 7 | 0 | 25 | 0 | 0 | 74.5 | 0.5 |
| 8 | 0 | 0 | 10 | 0 | 89.5 | 0.5 |
| 9 | 0 | 0 | 20 | 0 | 79.5 | 0.5 |
| 10 | 0 | 0 | 25 | 0 | 74.5 | 0.5 |
| 11 | 0 | 0 | 0 | 10 | 89.5 | 0.5 |
| 12 | 0 | 0 | 0 | 20 | 79.5 | 0.5 |
| 13 | 0 | 0 | 0 | 25 | 74.5 | 0.5 |

EXAMPLE 8

Crushing-strength studies

Binding characteristics of tablets

Figure 19:
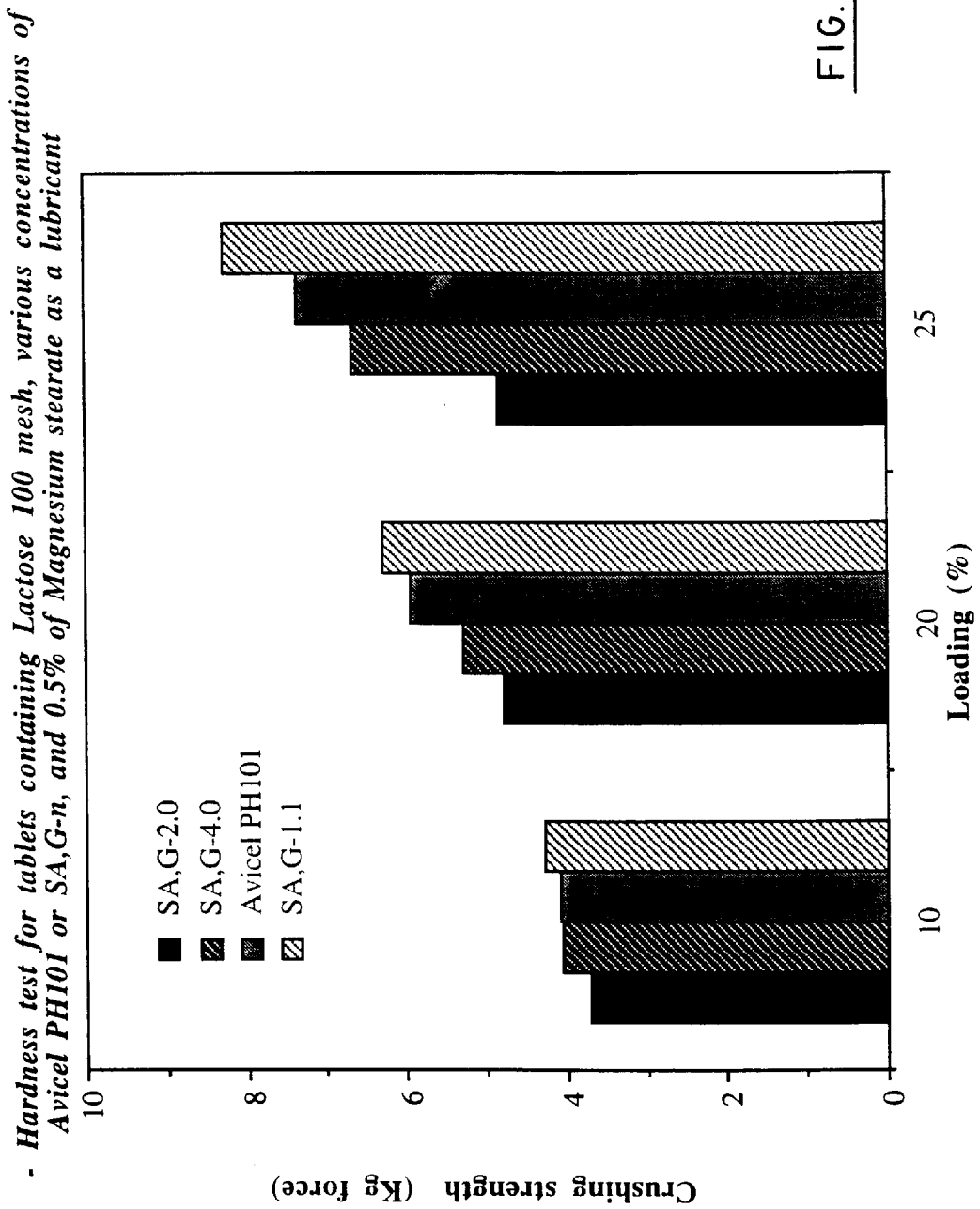
FIG. 19 is a diagram showing the crushing strength of SA,G-n tablets, as a function of the degree of substitution.

The crushing-strength of the tablets described in Example 7 was measured with the Amtrex Schleuniger-4M tablet hardness tester (Vector Corporation, Iowa, U.S.A.). Five tablets from each formulation were used in each determination and the mean values expressed in Kg force. The results are presented in Table 4 and FIG. 19.

The good influence of SA,G-n on the mechanical properties of the tablets are clearly demonstrated, specially when looking at the performances of the tablets containing Avicel-PH101®. The influence of the degree of substitution is also shown.

This example makes it clear that one may obtain by direct compression controlled release tablets with good mechanical properties. Such is another advantage of the use of substituted amylose.

TABLE 4

Hardness tests for tablets containing
various percentages of SA, G-n or AVICEL ®

| Polymer | % | \multicolumn{6}{c}{Crushing strength (Kg force)} |
|---|---|---|---|---|---|---|---|
| | | 1 | 2 | 3 | 4 | 5 | Mean |
| SA, G-1.1 | 0 | 3.8 | 4.1 | 3.4 | 3.7 | 4.1 | 3.8 ± 0.1 |
| | 10 | 4.3 | 4.3 | 4.0 | 4.5 | 4.3 | 4.3 ± 0.1 |
| | 20 | 6.6 | 5.8 | 5.6 | 6.8 | 6.5 | 6.3 ± 0.2 |
| | 25 | 7.6 | 8.2 | 9.2 | 8.3 | 8.2 | 8.3 ± 0.3 |
| SA, G-2.0 | 0 | 3.8 | 4.1 | 3.4 | 3.7 | 4.1 | 3.8 ± 0.1 |
| | 10 | 3.7 | 3.9 | 3.6 | 3.8 | 3.7 | 3.7 ± 0.1 |
| | 20 | 4.8 | 4.5 | 5.1 | 4.5 | 5.0 | 4.8 ± 0.1 |
| | 25 | 5.2 | 4.6 | 4.8 | 4.7 | 5.0 | 4.8 ± 0.1 |
| SA, G-4.0 | 0 | 3.8 | 4.1 | 3.4 | 3.7 | 4.1 | 3.8 ± 0.1 |
| | 10 | 4.2 | 4.0 | 4.0 | 3.9 | 4.2 | 4.0 ± 0.1 |
| | 20 | 5.0 | 5.2 | 5.2 | 5.4 | 5.6 | 5.3 ± 0.1 |
| | 25 | 6.6 | 6.5 | 6.8 | 6.8 | 6.5 | 6.7 ± 0.1 |
| Avicel PH 101 | 0 | 3.8 | 4.1 | 3.4 | 3.7 | 4.1 | 3.8 ± 0.1 |
| | 10 | 4.0 | 3.9 | 4.1 | 4.2 | 4.1 | 4.1 ± 0.1 |
| | 20 | 5.9 | 6.1 | 5.7 | 5.7 | 6.3 | 5.9 ± 0.1 |
| | 25 | 6.9 | 7.6 | 7.3 | 7.5 | 7.5 | 7.4 ± 0.1 |

EXAMPLE 9

Modification of the substituent (a) Synthesis of substituted amylose through 1,2-epoxybutane As aforesaid, substituted amylose can be prepared using other substituent than glycidol. In such cases, the controlled release properties of the final product will depend on the length of the chain R that will be grafted onto the amylose, the steric hindrance due to R, the presence of hydroxy groups on R or resulting from the reaction of the epoxy or other function, or the hydrophobicity of R.

1,2-epoxybutane was selected as a model of alternative substituent. The corresponding substituted amylose was prepared by reacting amylose with 1,2-epoxybutane in a strongly basic medium. Different degrees of substitution were obtained by simply varying the substituent/amylose ratio (mole of substitute/kg of amylose).

First, 50 g of amylose (Hylon® VII, National Starch and Chemical Company) were added to 300 ml of NaOH 1N heated to 50° C. The mixture was homogenized for 15 minutes in a Cafrano stirrer (type RZR50), at 800 rpm. 6 ml of 1,2-epoxybutane (Aldrich Chemical Company, St. Louis, USA, FW=72.11, d=0.837 g/ml) were added gradually and homogenization was continued for another 15 minutes at the same speed.

The obtained gel was then neutralized. 250 ml of distilled water heated to 50° C. was added. Thereafter, a sufficient amount of acetic anhydride was added in order to get a pH of 7.0. Homogenization was continued for another 5 minutes at the same speed.

The obtained gel was transferred equally into two separate 2 liter beakers. 300 ml of 85% acetone/water solution were added to each beaker and stirred manually. The content of each beaker was then washed through a Büchner funnel. The gel recovered from both beakers was washed twice with 300 ml of 40% acetone/water and finally three times more with 300 ml of 100% acetone. The resulting powder was exposed overnight to air.

One of the products prepared according to this example will be referred to hereinafter as SA,B-2.0 where SA means substituted amylose, B is a code for 1,2-epoxybutane and 2.0 represents the degree of substitution expressed as the ratio of mole of substituent per kilogram of amylose.

(b) preparation of the tablets

Acetaminophen was selected as a model for a release profile study of the above mentioned SA,B-20. Batches of tablets were prepared with the so prepared SA,B-2.0 and acetaminophen, with a drug percentage of 10% by weight.

The drug and the substituted amylose SA,B-2.0 were mixed manually in a mortar. Tablets weighing 400 mg each were compressed at a 2.5 tons/cm$^2$ pressure in an IR 30-tons press (C-30 Research & Industrial Instruments Company, London, U.K.). The diameter of the tablets was 1.26 cm.

(c) in vitro drug release from tablets

Tablets prepared as disclosed in paragraph (b) were placed individually in 900 ml of a phosphate buffer solution medium, pH=7.34, at 37° C., in U.S.P. XX dissolution apparatus equipped with a rotating paddle (50 rpm). The drug release was followed spectrophotometrically (acetaminophen: 242 nm) and continuously recorded. The drug release results were expressed using the equation as given hereinabove in example 3(b).

Each release profile was expressed as a plot of $M_t/M$ as function of the time (t). Each tablet formulation was tested in triplicate.

Figure 20:
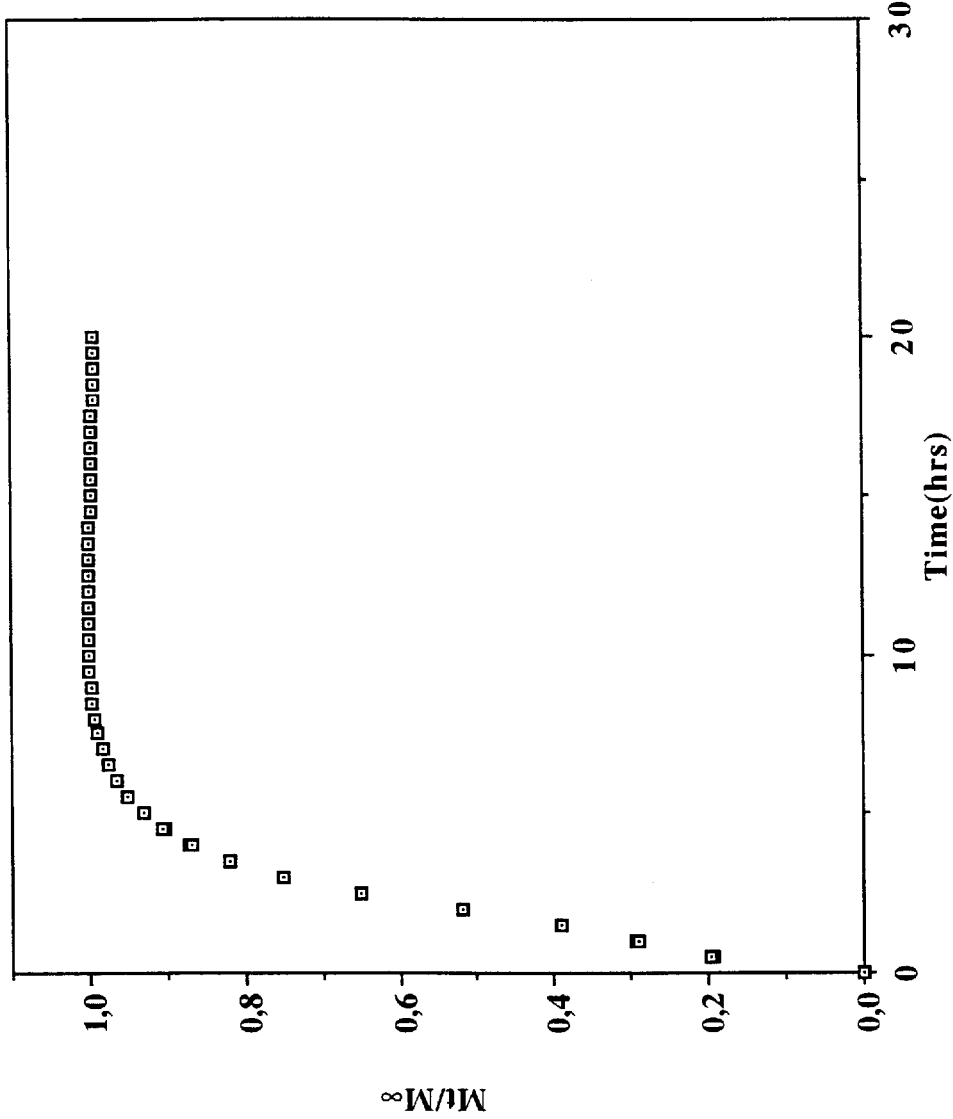
FIG. 20 is a diagram giving the fraction of acetaminophen released of SA,B-2.0 tablets containing the same, as a function of the time.

The results are presented in FIG. 20. A controlled release of the drug can be observed. More specifically, what was already observed for amylose substituted by glycidol can also be observed for amylose substituted by 1,2-epoxybutane.

EXAMPLE 10

Modification of the substituent (a) Synthesis of substituted amylose through 1,2-epoxydodecane Using the same proceeding as disclosed hereinabove in example 9(a), substituted amylose was prepared using 1,2-epoxydodecane as a model of alternative substituent. More specifically, substituted amylose was prepared by reacting amylose with 1,2-epoxydodecane (Aldrich Chemical Company, St. Louis, USA, FW=184.32, d=0.844 g/ml) in a strongly basic medium. Different degrees of substitution were obtained by simply varying the substitute/amylose ratio (mole of substitute /kg of amylose).

One of the products prepared according to this example will be referred to hereinafter as SA,D-2.0 where SA means substituted amylose, D is a code for 1,2-epoxydodecane and 2.0 represents the degree of substitution expressed as the ratio of mole of substituent per kilogram of amylose.

(b) preparation of the tablets

Acetaminophen was selected as a model for a release profile study of the above mentioned SA,D-2.0. Batches of tablets were prepared with the substituted amylose polymer, SA,D-2.0 and acetaminophen, as drug, with a drug percentage of 10% by weight.

The drug and the substituted amylose SA,D-2.0 were mixed manually in a mortar. Tablets weighing 400 mg each were compressed at a 2.5 tons/cm$^2$ pressure in an IR 30-tons press (C-30 Research & Industrial Instruments Company, London, U.K.). The diameter of the tablets was 1.26 cm.

(c) in vitro drug release from tablets

Tablets prepared as disclosed in paragraph (b) were placed individually in 900 ml of a phosphate buffer solution medium, pH=7.34, at 37° C., in an U.S.P. XX dissolution apparatus equipped with a rotating paddle (50 rpm). The drug release was followed spectrophotometrically (acetaminophen: 242 nm) and continuously recorded. The drug release results were expressed using the equation as given in example 3(b).

Thus, each release profile was expressed as a plot of $M_t/M$ as a function of the time (t). Each tablet formulation was tested in triplicate.

Figure 21:
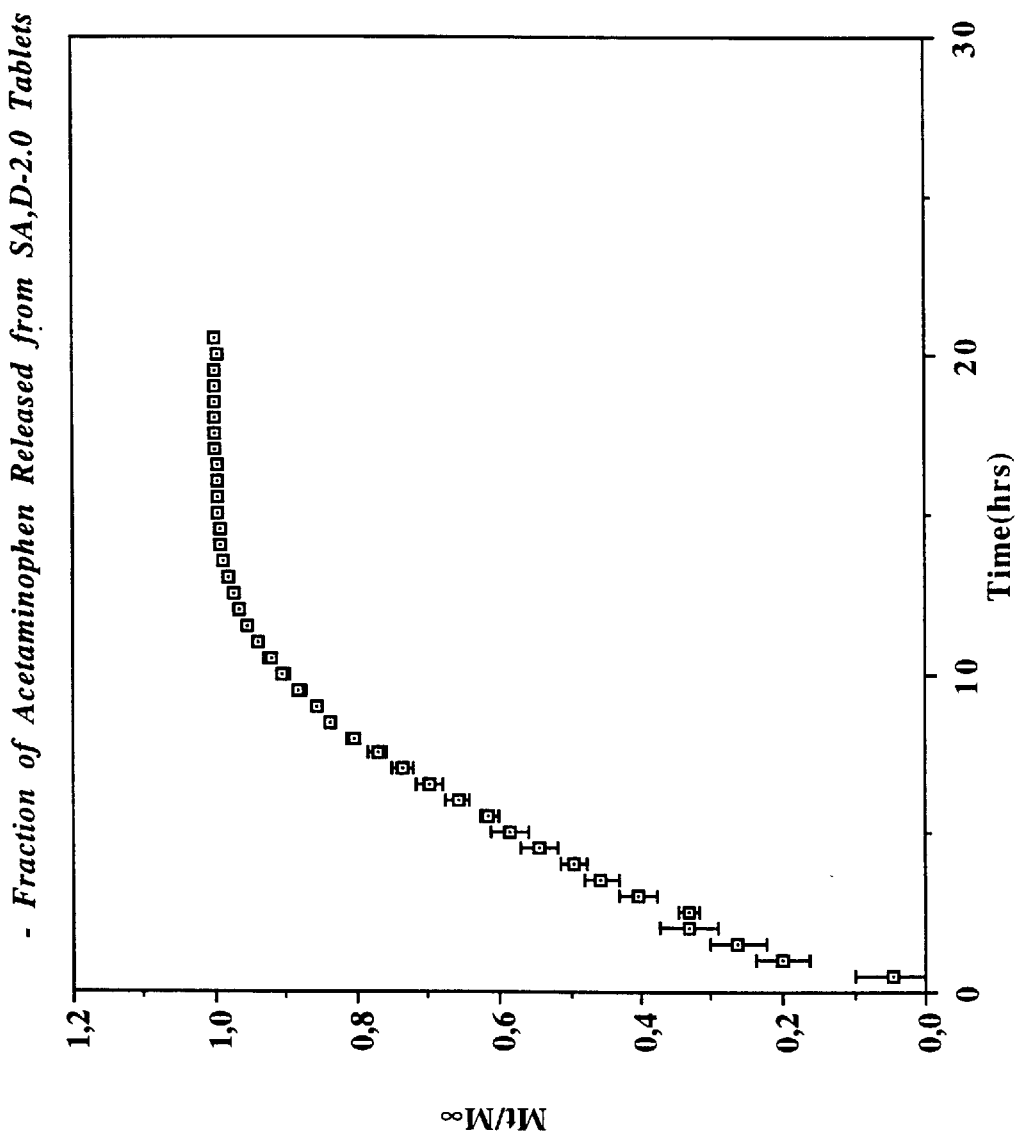
FIG. 21 is a diagram giving the fraction of acetaminophen released from SA,D-2.0 tablets as a function of the time.

The results are presented in FIG. 21. Once again, a controlled release of the drug was observed. Also, it is possible to see the effect of the chain length and its hydrophobicity by comparing the results in FIGS. 20 and 21. The hydrophobicity decreases the penetration of the water into the tablet and decreases the release rate of the drug.

If a comparison is now made with the result obtained with SA,G-2.0 (see FIG. 6), one can see that the absence of OH terminal groups in the substituent chain seems to decrease the interactions between the macromolecular chains and thus the viscosity, which leads to a small decrease in the release time as compared to SA,G-2.0. In any event, a high potential exists for the use of substituents which would be selected as a function of the hydrophobicity of the drug to be released.

EXAMPLE 11

Modification of the substituent (a) Synthesis of substituted amylose through 1-chlorobutane The synthesis of substituted amylose through a halide function was investigated.

Using the substantially same proceeding as disclosed hereinabove in Example 9(a), substituted amylose was prepared using 1-chlorobutane as a model of alternative substituent. The only difference in the synthesis process was that before the addition of the reactant, the pH was adjusted to a slight alkalinity to avoid degradation of said reactant.

Different degrees of substitution were obtained by simply varying the substituent to amylose ratio (mole of substitute/kg of amylose).

Two products prepared according to this example will be referred to hereinafter as SA, C-2.7 and SA, C-5.4, respectively where SA means substituted amylose, C is a code for 1-chlorobutane and 2.7 and 5.4 represent two degrees of substitution expressed as the ratio of mole of substituent per kilogram of amylose.

(b) preparation of the tablets

Acetaminophen was selected as a model for a release profile study of the above mentioned SA, C-2.7 and SA, C-5.4. Batches of tablets were prepared with these two substituted amylose polymers and acetaminophen as drug, with a drug percentage of 10% by weight.

The drug and the substituted amylose SA, C-2.7 and SA, C-5.4 were mixed manually in a mortar. Tablets weighing 400 mg each were compressed at a 2.5 tons/cm$^2$ pressure in an IR 30-tons press (C-30 Research & Industrial Instruments Company, London, U.K.). The diameter of the tablets was 1.26 cm.

(c) in vitro drug release from tablets

Tablets prepared as disclosed in paragraph (b) were placed individually in 900 ml of a phosphate buffer solution medium, pH=7.34, at 37° C., in an U.S.P. XX dissolution apparatus equipped with a rotating paddle (50 rpm). The drug release was followed spectrophotometrically (acetaminophen; 242 nm) and continuously recorded. The drug release results were expressed using the equation as given in example 3(b).

Thus, each release profile was expressed as a plot of $M_t/M$ as a function of the time (t). Each tablet formulation was tested in triplicate.

Figure 22:
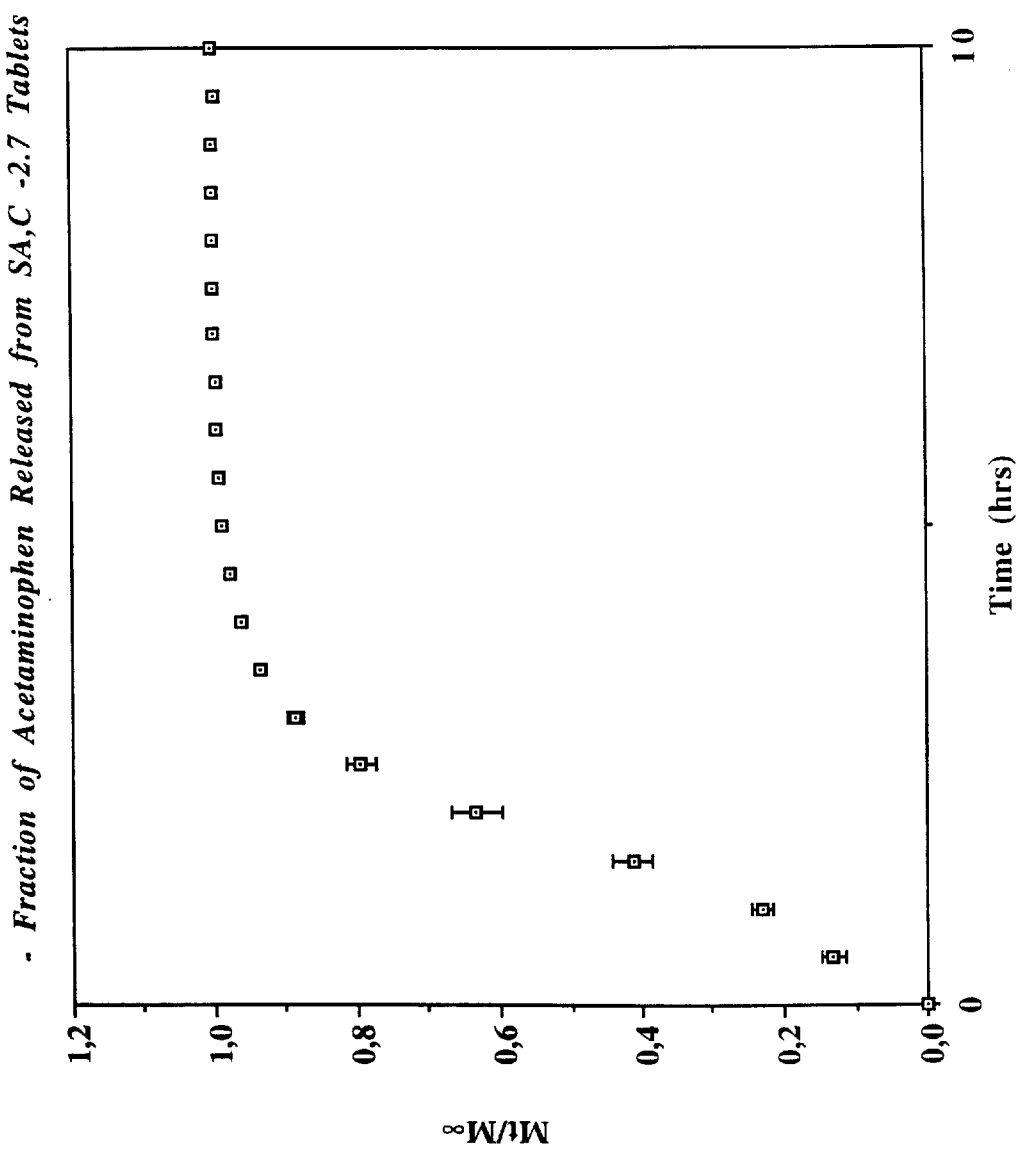
FIG. 22 is a diagram giving the fraction of acetaminophen released from SA, C-2.7 tablets, as a function of the time.
Figure 23:
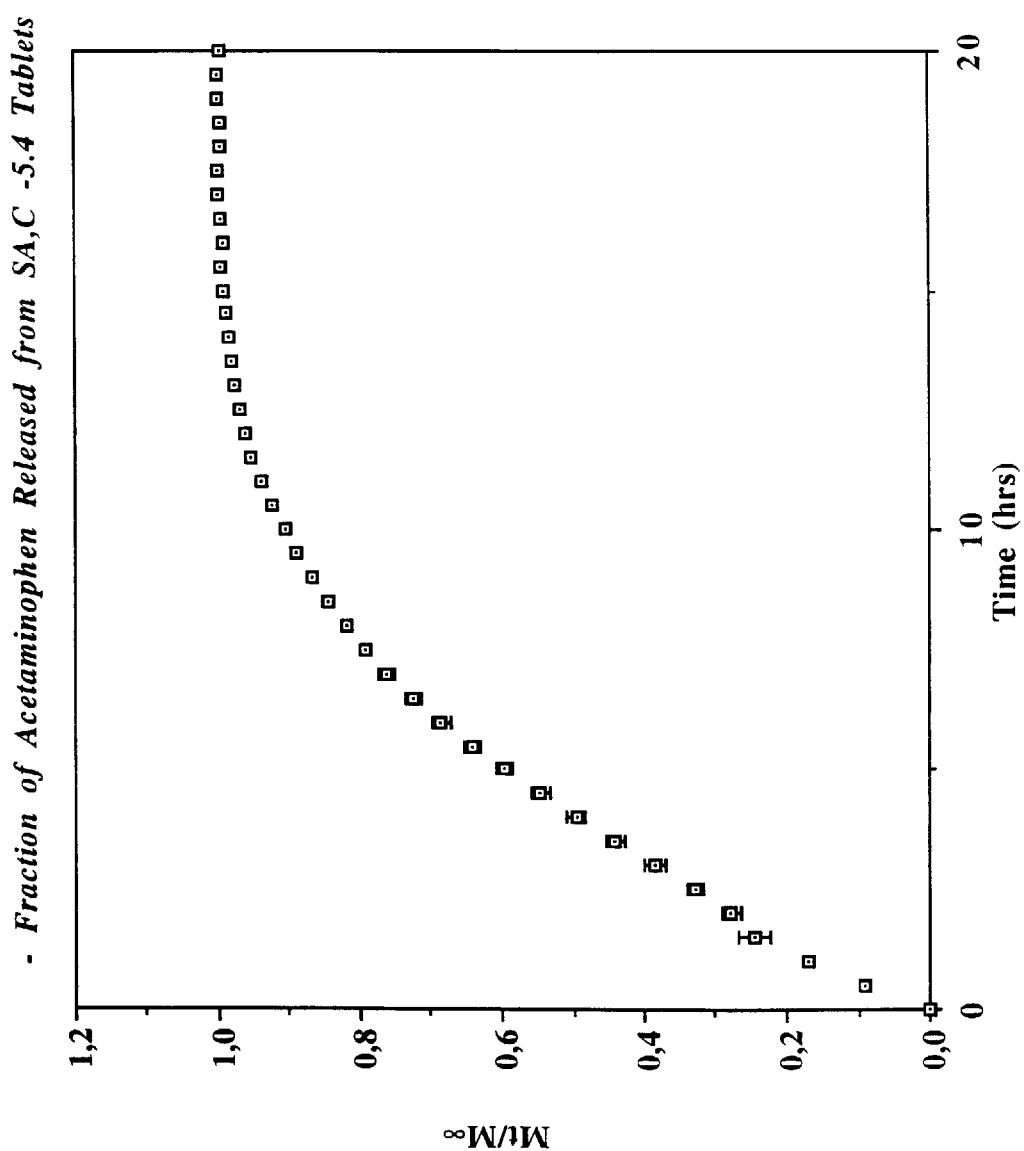
FIG. 23 is a diagram giving the fraction of acetaminophen released from SA, C-5.4 tablets, as a function of the time.

The results are presented in FIGS. 22 and 23. Once again, a good controlled release of the drug was observed.

One can also see that the rate of drug delivery depends on the degree of substitution. This clearly demonstrates that one can use any suitable function which is able to react with the hydroxy groups located on the amylose molecule to finally obtain substituted amylose.

EXAMPLE 12

Effect of the tablet drug loading on the in vitro tablet release profile

Using the very same proceedings as disclosed hereinabove in Example 4, tablets containing 70 and 80% by weight of hydrocortisone as a drug to be released and SA, G-2.7 as a matrix for the drug, were prepared and tested.

Figure 24:
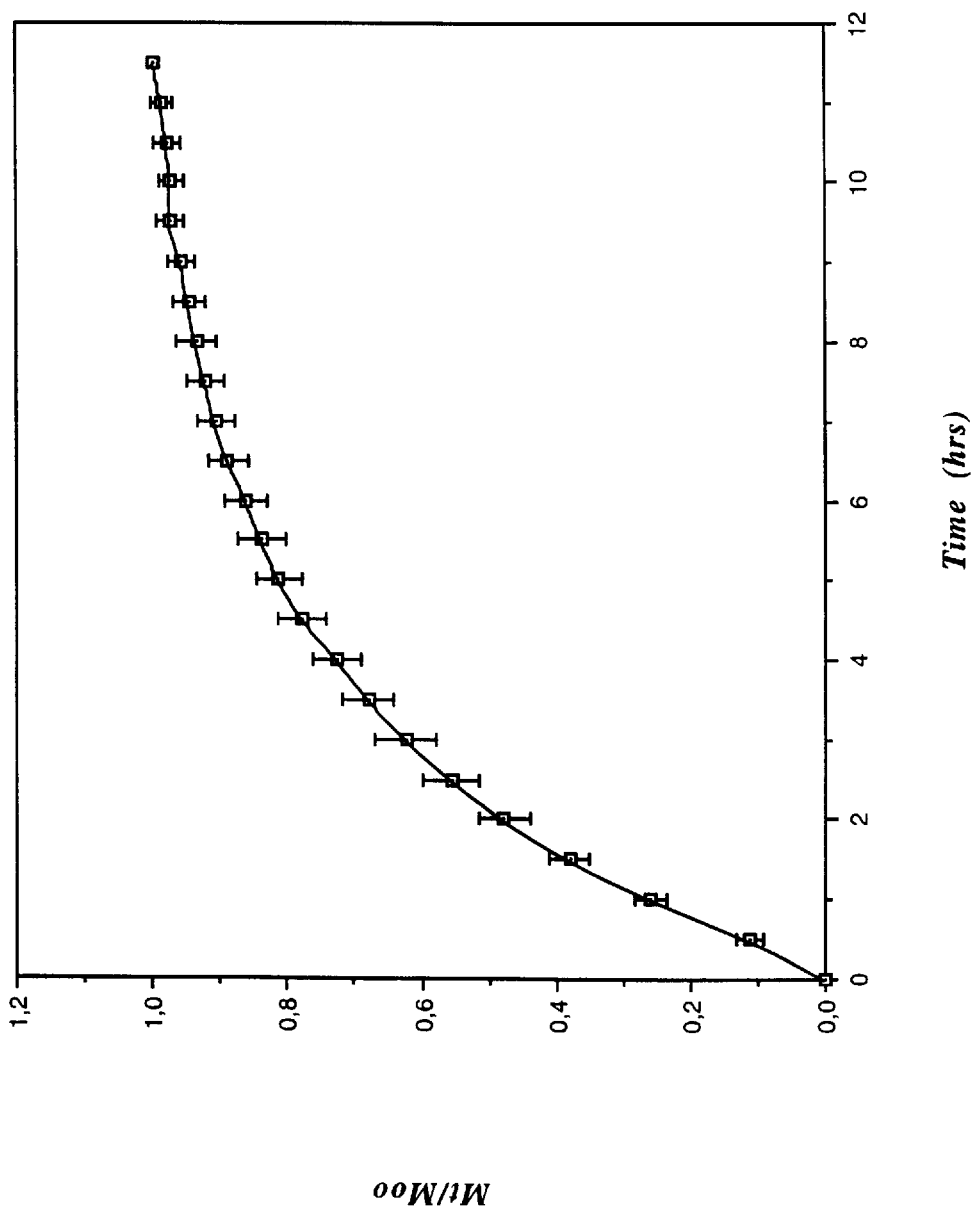
FIG. 24 is a diagram showing the fraction of hydrocortisone released from SA, G-2.7 tablets containing 70% of the same, as a function of the time.
Figure 25:
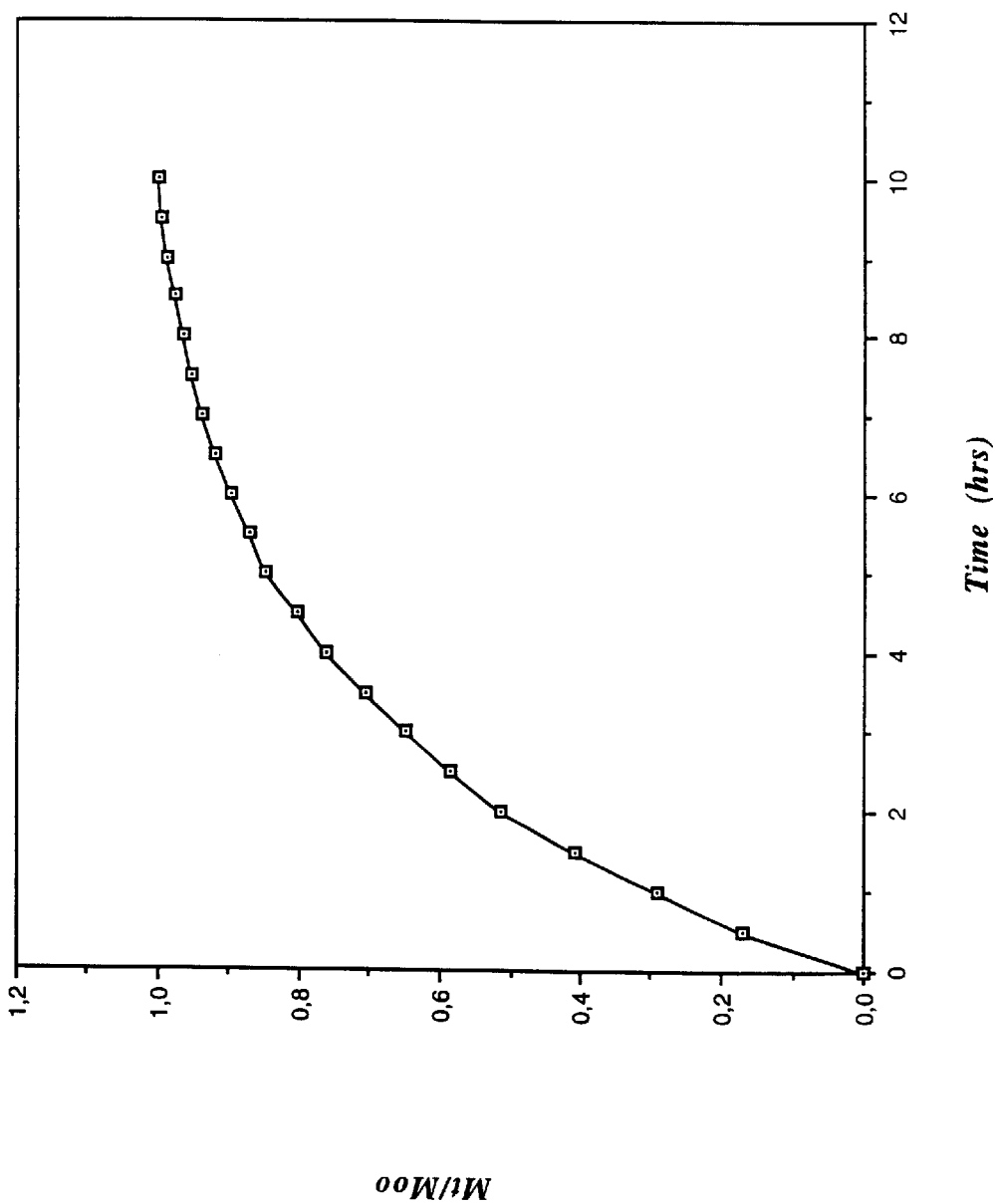
FIG. 25 is a diagram showing the fraction of hydrocortisone released from SA, G-2.7 tablets containing 80% of the same, as a function of the time.

The results that were so obtained as presented in FIGS. 24 and 25. As can be seen, even with up to 80% of drug within the tablets, an excellent controlled release was obtained. Such is quite unusual in tablets prepared by direct compression with such a high amount of drug.

As a matter of fact, it appears that drug release control is achieved not only through diffusion and swelling, but also through physical erosion.

EXAMPLE 13

Dry-coated tablets

Dry coated tablets using substituted amylose as a matrix were prepared by direct compression.

The cores of such tablets were prepared by compressing a mixture of 95 mg of acetaminophen with 5 mg of SA, G-5.4 in an IR 30 tons press.

Then, the cores were placed on a polymer powder bed made in a die, and were covered with the same polymer powder, so as to form a core-surrounding shell.

The core-shell system was then compressed in the dye, thereby giving the requested dry-coated tablets.

As a shell-forming polymer powder, use was made of SA, G-2.0 and SA, G-2.7, respectively, in an amount of about 200 mg per tablet.

The dry-coated tablets that were so prepared were tested in vitro, using the same proceedings as disclosed in all the previous examples.

Figure 26:
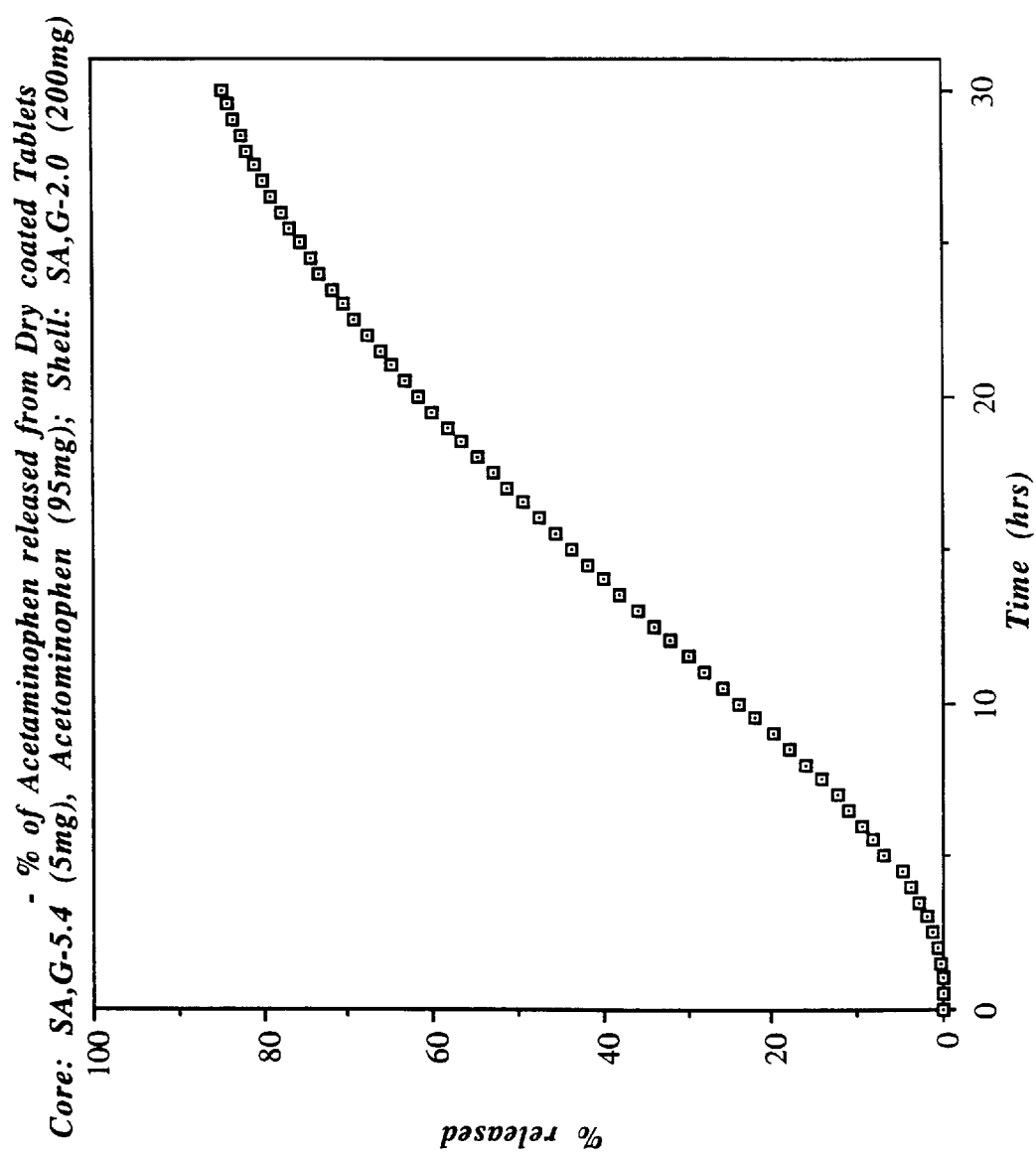
FIG. 26 is a diagram giving the fraction of acetaminophen released from dry-coated tablets having a shell made of SA, G-2.0, as a function of the time.
Figure 27:
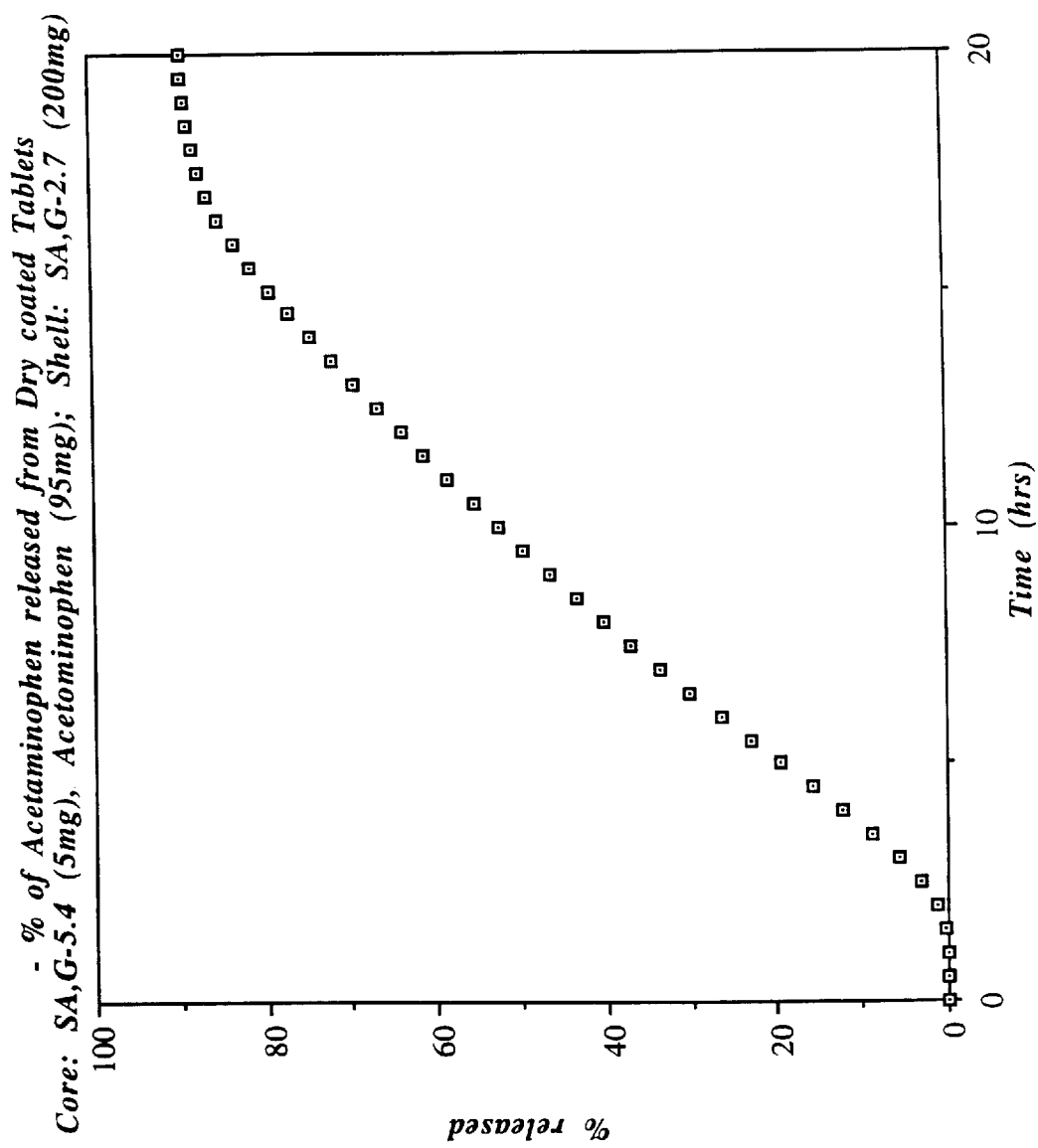
FIG. 27 is a diagram giving the fraction of acetaminophen released from dry-coated tablets having a shell made of SA, G-2.7, as a function of the time.

The obtained results are reported in FIGS. 26 and 27. As can be seen, good release control was obtained in both cases. This makes it clear that in accordance with the invention, one may incorporate very large amounts of drug in a tablet and still obtain very good release control.

Of course, numerous modifications could be made to the above invention as it was disclosed and exemplified, without departing from the scope of the appended claims.

We claim:

1. A pharmaceutical sustained release tablet for oral administration, consisting essentially of non-crystalline, a compressed blend of at least two dry powders including a powder of at least one pharmaceutical drug and a powder of a sustained release matrix for the drug, wherein said sustained release matrix consists of uncrosslinked substituted amylose prepared by reacting in a basic medium, amylose with at least one organic substituent having a reactive function that reacts with the hydroxy groups of the amylose molecule.

2. The tablet of claim 1, wherein the blend of dry powders also includes a lubricant powder.

3. The tablet of claim 2, wherein the lubricant is magnesium stearate.

4. The tablet of claim 2, wherein the blend of dry powders further includes a filler powder.

5. The tablet of claim 2, wherein the filler is lactose.

6. The tablet of claim 1, wherein the substituted amylose has a substituent to amylose ratio (expressed in mole of substituent per kg of amylose) that is equal to or higher than 0.4.

7. The tablet of claim 1, wherein the substituted amylose has a substituent to amylose ratio (expressed in mole of substituent per kg of amylose) that ranges from 0.4 to 7.0.

8. The tablet of claim 1, wherein the organic substituent is selected from the group consisting of epoxy alkanes, epoxy alcohols, epoxy ethers, epoxy aryls, cycloalkene oxides, halogeno alkanes, halogeno alcohols, and alkyl and aryl isocyanates.

9. A pharmaceutical sustained release tablet for oral administration, consisting of a compressed blend of at least two dry powders including a powder of at least one pharmaceutical drug and a powder of a sustained release matrix for the drug, wherein said sustained release matrix consists essentially of non-crystalline, uncrosslinked substituted amylose prepared by reacting in a basic medium, amylose with at least one organic substituent having a reactive function that reacts with the hydroxy groups of the amylose molecule, wherein the reactive function of the substituent is an epoxy group.

10. The tablet of claim 9, wherein the organic substituent is 1,2-epoxypropanol.

11. The tablet of claim 9, wherein the organic substituent is 1,2-epoxybutane.

12. The tablet of claim 9, wherein the organic substituent is 1,2-epoxydodecane.

13. A pharmaceutical sustained release tablet for oral administration, consisting of a compressed blend of at least two dry powders including a powder of at least one pharmaceutical drug and a powder of a sustained release matrix for the drug, wherein said sustained release matrix consists essentially of non-crystalline, uncrosslinked substituted amylose prepared by reacting in a basic medium, amylose with at least one organic substituent having a reactive function that reacts with the hydroxy groups of the amylose molecule wherein the reactive function of the substituent is a halide.

14. The tablet of claim 13, wherein the organic substituent is 1-chlorobutane.

15. A pharmaceutical sustained release tablet for oral administration, consisting of a compressed blend of at least two dry powders including a powder of at least one pharmaceutical drug and a powder of a sustained release matrix for the drug, wherein said sustained release matrix consists essentially of non-crystalline, uncrosslinked substituted amylose prepared by reacting in a basic medium, amylose with at least one organic substituent having a reactive function that reacts with the hydroxy grounds of the amylose molecule, wherein the reactive function of the substituent is an isocyanate group.

16. The tablet of claim 6, wherein:

said at least one pharmaceutical drug is very slightly soluble; and said powder of said at least one pharmaceutical drug represents up to 80% by weight of the whole tablet.

17. The tablet of claim 6, wherein:

said at least one pharmaceutical drug is very soluble; and said powder of said at least pharmaceutical drug represents up to 40% by weight of the whole tablet.

18. The tablet of claim 6, wherein:

said tablet is a dry coated tablet including a core surrounded by a shell;

said core includes said powder of said at least one pharmaceutical drug; and said shell is made of said powder of said sustained release matrix consisting of substituted amylose.

19. The tablet of claim 6, wherein:

said tablet is a dry coated tablet including a core surrounded by a shell.

20. The tablet of claim 1, wherein the substituent is phosphorus oxychloride.

* * * * *

UNITED STATES PATENT AND TRADEMARK OFFICE
CERTIFICATE OF CORRECTION

PATENT NO.    : 5,879,707
DATED         : March 9, 1999
INVENTOR(S)   : Cartilier et al.

It is certified that error appears in the above-identified patent and that said Letters Patent is hereby corrected as shown below:

Title page,
Item [57], ABSTRACT,
Line 10, please replace with the following:
-- alcohol. With such a matrix, controlled and sustained release --.

Column 2,
Line 2, please delete "100,00" and insert -- 100,000 --;
Line 12, please delete "amyollytic" and insert -- amylolitic --;
Line 61, please delete "hydrophillic" and insert -- hydrophilic --.

Column 9,
Line 9, please delete "B";
Line 10, please cancel "üchner" and insert -- Büchner --.

Column 10,
Lines 2 and 9, please cancel "evermore" and insert -- evenmore --.

Column 11,
Line 33, please cancel after 2.5 "ton/cm$^2$" and insert -- tons/cm$^2$ --;
Lines 51, 53 and 56, please cancel "M" and insert -- $M_\infty$ --.

Column 12,
Line 44, please cancel "M" and insert -- $M_\infty$ --.

Column 16,
Line 38, please cancel "SA,B-20" and insert -- SA,B-2.0 --;
Line 55, please cancel "M" and insert -- $M_\infty$ --.

Column 17,
Line 35, please cancel "M" and insert -- $M_\infty$ --.

Column 18,
Line 28, please cancel "M" and insert -- $M_\infty$ --.

UNITED STATES PATENT AND TRADEMARK OFFICE
CERTIFICATE OF CORRECTION

PATENT NO. : 5,879,707
DATED : March 9, 1999
INVENTOR(S) : Cartilier et al.

It is certified that error appears in the above-identified patent and that said Letters Patent is hereby corrected as shown below:

Column 19,
Line 20, please cancel "essentially of non-crystalline" and insert -- of --;
Line 24, please cancel "of" and insert -- essentially of non-crystalline --.

Signed and Sealed this

Eighteenth Day of March, 2003

JAMES E. ROGAN
*Director of the United States Patent and Trademark Office*